(12) United States Patent
Myles et al.

(10) Patent No.: US 10,682,379 B2
(45) Date of Patent: Jun. 16, 2020

(54) USE OF GRAM NEGATIVE SPECIES TO TREAT ATOPIC DERMATITIS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Ian Antheni Myles, Bethesda, MD (US); Sandip K. Datta, Bethesda, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/249,721

(22) Filed: Jan. 16, 2019

(65) Prior Publication Data

US 2019/0142874 A1    May 16, 2019

Related U.S. Application Data

(60) Continuation of application No. 16/014,971, filed on Jun. 21, 2018, now Pat. No. 10,206,957, which is a division of application No. 15/939,066, filed on Mar. 28, 2018, now Pat. No. 10,195,236, which is a continuation of application No. PCT/US2017/028133, filed on Apr. 18, 2017.

(60) Provisional application No. 62/324,762, filed on Apr. 19, 2016.

(51) Int. Cl.
| | |
|---|---|
| *A61K 35/74* | (2015.01) |
| *A61P 17/04* | (2006.01) |
| *A61K 9/00* | (2006.01) |
| *A61K 9/06* | (2006.01) |

(52) U.S. Cl.
CPC ............ *A61K 35/74* (2013.01); *A61K 9/0014* (2013.01); *A61K 9/06* (2013.01); *A61P 17/04* (2018.01)

(58) Field of Classification Search
CPC ........ A61K 9/0014; A61K 35/74; A61K 9/06; A61P 17/04
See application file for complete search history.

(56) References Cited

U.S. PATENT DOCUMENTS

| | | |
|---|---|---|
| 3,832,253 A | 8/1974 | Di Palma et al. |
| 3,854,480 A | 12/1974 | Zaffaroni |
| 4,452,775 A | 6/1984 | Kent |
| 4,667,014 A | 5/1987 | Nestor, Jr. et al. |
| 4,748,034 A | 5/1988 | De Rham |
| 4,829,000 A | 5/1989 | Kleinman et al. |
| 5,239,660 A | 8/1993 | Ooi |
| 6,218,371 B1 | 4/2001 | Krieg et al. |
| 6,974,585 B2 | 12/2005 | Askill |
| 8,481,299 B2 | 7/2013 | Gueniche et al. |
| 9,173,910 B2 | 11/2015 | Kaplan et al. |
| 1,019,523 A1 | 2/2019 | Myles et al. |
| 1,020,695 A1 | 2/2019 | Myles et al. |
| 2012/0165357 A1 | 6/2012 | Hung et al. |
| 2013/0121968 A1 | 5/2013 | Quay |
| 2013/0273144 A1 | 10/2013 | Maj et al. |
| 2016/0192580 A1 | 7/2016 | Myles et al. |
| 2016/0235792 A1 | 8/2016 | Berry et al. |
| 2016/0317653 A1 | 11/2016 | Cook et al. |
| 2017/0202889 A1 | 7/2017 | Lang et al. |
| 2018/0325968 A1 | 11/2018 | Morris et al. |
| 2018/0360891 A1 | 12/2018 | Myles et al. |

FOREIGN PATENT DOCUMENTS

| | | |
|---|---|---|
| EP | 1786445 A2 | 5/2007 |
| JP | 2006131622 A | 5/2006 |
| WO | WO-9510999 A1 | 4/1995 |
| WO | WO-03033660 A2 | 4/2003 |
| WO | WO-03047533 A2 | 6/2003 |
| WO | WO-2006036406 A2 | 4/2006 |
| WO | WO-2006048747 A1 | 5/2006 |
| WO | WO-2012150269 A1 | 11/2012 |
| WO | WO-2013153358 A1 | 10/2013 |
| WO | WO-2016172196 A1 | 10/2016 |
| WO | WO-2017184601 A1 | 10/2017 |

OTHER PUBLICATIONS

Cyzeska F.J. et al., "Culture Medium for Selective Isolation and Enumeration of Gram-Negative Bacteria from Ground Meats", Applied and Environmental Microbiology, Aug. 1981, vol. 42, No. 2, pp. 303-307. (Year: 1981).*

Dekio I. et al., "Characterization of skin microbiota in patients with atopic dermatitis and in normal subjects using 16S rRNA gene-based comprehensive analysis", Journal of Medical Microbiology, 2007, vol. 56, pp. 1675-1683. (Year: 2007).*

Adjide C.C. et al., "A sensitive, specific and predictive isolation medium developed for Stenotrophomonas maltophilia study in healthcare settings", Pathol Biol (Paris). 2010, vol. 58, No. 1, pp. 11-7; doi: 10.1016/j.patbio.2009.07.004. (ENGLISH ABSTRACT ONLY; total 2 pages provided) (Year: 2010).*

Furuhata K. et al., "Characteristics of a Pink-Pigmented Bacterium Isolated from Biofilm in a Cooling Tower in Tokyo, Japan", Microbiol. Immunol., 2007, vol. 51, No. 6, pp. 637-641. (Year: 2007).*

(Continued)

*Primary Examiner* — Satyendra K Singh
(74) *Attorney, Agent, or Firm* — Wilson Sonsini Goodrich & Rosati

(57) ABSTRACT

Pharmaceutical compositions are disclosed that includes a therapeutically effective amount of a purified viable gram negative bacteria and a pharmaceutically acceptable carrier. The pharmaceutical compositions are formulated for topical administration. Methods of treating atopic dermatitis using these pharmaceutical compositions are also disclosed.

15 Claims, 11 Drawing Sheets

(56) References Cited

OTHER PUBLICATIONS

O'Doherty A. et al., "Development of nalidixic acid amphotericin B vancomycin (NAV) medium for the isolation of Campylobacter ureolyticus from the stools of patients presenting with acute gastroenteritis", British Journal of Biomedical Sciences, 2014, vol. 71, No. 1, pp. 6-12. (Year: 2014).*
Abbasi. Are Bacteria Transplants the Future of Eczema Therapy? JAMA pp. E1-E2 (Aug. 29, 2018).
Asher et al. Worldwide time trends in the prevalence of symptoms of asthma, allergic rhinoconjunctivitis, and eczema in childhood: ISAAC Phases One and Three repeat multicountry cross-sectional surveys. Lancet 368:733-743 (2006).
Avis. Chapter 87: Parenteral Preparations. Remington: The Science and Practice of Pharmacy, 19th Ed. (Easton, PA: Mack Publishing Co.) (p. 1530) (1995).
Bantz et al. The Atopic March: Progression from Atopic Dermatitis to Allergic Rhinitis and Asthma. J Clin Cell Immunol 5(2):202 (2014).
Barnes et al. An update on the genetics of atopic dermatitis: scratching the surface in 2009. J Allergy Clin Immunol 125:16-31 (2010).
Bilal et al. Pattern of Bacterial Colonization of Atopic Dermatitis in Saudi Children. J Clin Diagn Res. 7(9):1968-1970 (2013).
Bin et al. Genetic and epigenetic studies of atopic dermatitis. Allergy Asthma Clin Immunol 12:52 (2016).
Bogdanffy et al. Metabolism of Dibasic Esters by Rat Natal Mucosal Carboxylesterase. Drug Metab Dispos 19(1):124-129 (1991).
Boguniewicz et al. Recent insights into atopic dermatitis and implications for management of infectious complications. J Allergy Clin Immunol 125(1):4-19 (2010).
Boguniewicz et al. The ABC's of managing patients with severe atopic dermatitis. J Allergy Clin Immunol 132(2):511-2.e5 (2013).
Brauweiler et al. The cytokines increase *Staphylococcus aureus* alpha toxin-induced keratinocyte death through the signal transducer and activator of transcription 6 (STAT6). J Invest Dermatol 134(8):2114-2121 (2014).
Co-pending U.S. Appl. No. 16/184,498, filed Nov. 8, 2018.
Co-pending U.S. Appl. No. 16/244,903, filed Jan. 10, 2019.
Co-pending U.S. Appl. No. 16/271,552, filed Feb. 8, 2019.
Co-pending U.S. Appl. No. 16/271,577, filed Feb. 8, 2019.
Czarnowicki et al. Novel concepts of prevention and treatment of atopic dermatitis through barrier and immune manipulations with implications for the atopic march. J Allergy Clin Immunol 139(6):1723-1734 (2017).
Dé et al. Clinical significance of *Roseomonas* species isolated from catheter and blood samples: analysis of 36 cases in patients with cancer. Clin Infect Dis 38(11):1579-1584 (2004).
Di Nardo et al. Ceramide and cholesterol composition of the skin of patients with atopic dermatitis. Acta Derm Venereol 78(1):27-30 (1998).
Dinulos et al. New science and treatment paradigms for atopic dermatitis. Curr Opin Pediatr 30(1):161-168 (2018).
Dolgin. First eczema biologic debuts but price could restrict use. Nat Biotechnol 35(5):391-392 (2017).
Dréno et al. Microbiome in healthy skin, update for dermatologists. J Eur Acad Dermatol Venereol 30(12):2038-2047 (2016).
Eichenfield et al. Current guidelines for the evaluation and management of atopic dermatitis: A comparison of the Joint Task Force Practice Parameter and American Academy of Dermatology guidelines. J Allergy Clin Immunol 139(45):S49-S57 (2017).
Eichenfield et al. Guidelines of Care for the Management of Atopic Dermatitis: Part 2: Management and Treatment of Atopic Dermatitis with Topical Therapies. J Am Acad Dermatol 71(1):116-132 (2014).
Follin et al. A skin chamber technique as a human model for studies of aseptic inflammatory reactions. Method Mol Biol 412:333-346 (2007).
Gerding et al. Administration of Spores of Nontoxigenic Clostridium difficile Strain M3 for Prevention of Recurrent C difficile Infection: A Randomized Clinical Trial. JAMA 313(17):1719-1727 (2015).
Gittler et al. Bathing and Associated Treatment in Atopic Dermatitis. Am J Clin Dermatol 18:45-57 (2017).
Grice et al. The Skin Microbiome. Nature 9:244-253 (2011).
Gueniche et al. Effects of nonpathogenic gram-negative bacterium *Vitreoscilla filiformis* lysate on atopic dermatitis: a prospective, randomized, double-blind, placebo-controlled clinical study. Br J Dermatol 159:1357-1363 (2008).
Henderson et al. The burden of disease associated with filaggrin mutations: a population-based, longitudinal birth cohort study. J Allergy Clin Immunol 121(4):872-877.e9 (2008).
Hon et al. Barrier repair therapy in atopic dermatitis: an overview. Am J Clin Dermatol 14(5):389-399 (2013).
Hsu et al. Intermediate phenotypes in patients with autosomal dominant hyper-IgE syndrome caused by somatic mosaicism. J Allergy Clin Immunol 131(6):1586-1593 (2013).
Hwang et al. Prevalence of atopic dermatitis, allergic rhinitis and asthma in Taiwan: a national study 2000 to 2007. Acta Derma Venereol 90(6):589-594 (2010).
Inami et al. Surfactant-induced Chronic Pruritus: Role of L-Histidine Decarboxylase Expression and Histamine Production in Epidermis. Acta Derm Venereol 94:645-650 (2014).
Inoshima et al. A *Staphylococcus aureus* pore-forming toxin subverts the activity of ADAM10 to cause lethal infection in mice. Nature 17(10):1310-1315 (2011).
Janmohamed et al. The proactive wet-wrap method with diluted corticosteroids versus emollients in children with atopic dermatitis: a prospective, randomized, double-blind, placebo-controlled trial. J Am Acad Dermatol 70(6):1076-1082 (2014).
Jensen et al. Impaired Sphingomyelinase Activity and Epidermal Differentiation in Atopic Dermatitis. J Invest Dermatol 122(6):1423-1431 (2004).
Kobayashi et al. Dysbiosis and *Staphylococcus aureus* Colonization Drives Inflammation in Atopic Dermatitis. Immunity 42(4):756-766 (2015).
Kolls et al. Cytokine-mediated regulation of antimicrobial proteins. Nat Rev Immunol 8(11):829-835 (2008).
Kong et al. Temporal shifts in the skin microbiome associated with disease flares and treatment in children with atopic dermatitis. Genome Res 22(5):850-859 (2012).
Krämer et al. Seasonality in symptom severity influenced by temperature or grass pollen: results of a panel study in children with eczema. J Invest Dermatol 124(3):514-523 (2005).
Kubo et al. Epidermal barrier dysfunction and cutaneous sensitization in atopic diseases. J Clin Invest 122(2):440-447 (2012).
Latvala et al. Trends in prevalence of asthma and allergy in Finnish young men: nationwide study, 1966-2003. BMJ 330(7501):1186-1187 (2005).
Lau et al. A rapid matrix-assisted laser desorption ionization-time of flight mass spectrometry-based method for single-plasmid tracking in an outbreak of carbapenem-resistant Enterobacteriaceae. J Clin Microbiol 52:2804-2812 (2014).
Lau et al. Development of a clinically comprehensive database and a simple procedure for identification of molds from solid media by matrix-assisted laser desorption ionization-time of flight mass spectrometry. J Clin Microbiol 51:828-834 (2013).
Leloup et al. Outpatient Home-based Wet Wrap Dressings with Topical Steroids with Children with Severe Recalcitrant Atopic Dermatitis: A Feasibility Pilot Study. Pediatr Dermatol 32(4):e177-178 (2015).
Lewis-Jones. Quality of life and childhood atopic dermatitis: the misery of living with childhood eczema. Int J Clin Pract 60(8):984-992 (2006).
Li et al. Altered composition of epidermal lipids correlates with *Staphylococcus aureus* colonization status in atopic dermatitis. Br J Dermatol 177(4):e125-e127 (2017).
Li et al. Topical vitamin D3 and low-calcemic analogs induce thymic stromal lymphopoietin in mouse keratinocytes and trigger an atopic dermatitis. PNAS USA 103(31):11736-11741 (2006).
Lyons et al. Atopic dermatitis in children: clinical features, pathophysiology, and treatment. Immunol Allergy Clin North Am 35:161-183 (2015).
Margolis et al. Persistence of mild to moderate atopic dermatitis. JAMA Dermatol. 150(6):593-600 (2014).

(56) References Cited

OTHER PUBLICATIONS

Mennini et al. Two Phase 3 Trials of Dupilumab versus Placebo in Atopic Dermatitis. N Engl J Med 376(11):1090 (2017).
Michon et al. Bacteremia due to imipenem-resistant Roseomonas mucosa in a child with acute lymphoblastic leukemia. J Pediatr Hematol Oncol. 36(3):e165-168 (2014).
Miller et al. Vitamin D and innate immunity. Dermatol Ther 23:13-22 (2010).
Miyamoto-Shinohara et al. Survival of freeze-dried bacteria. J Gen Appl Microbiol 54(1):9-24 (2008).
Msika et al. New emollient with topical corticosteroid-sparing effect in treatment of childhood atopic dermatitis: SCORAD and quality of life improvement. Pediatr Dermatol 25(6):606-612 (2008).
Muthuri et al. Impact of neuraminidase inhibitors on influenza A(H1N1)pdm09-related pneumonia: an individual participant data meta-analysis. Influenza Other Respir Viruses 10(3):192-204 (2016).
Myles et al. A method for culturing Gram-negative skin microbiota. BMC Microbiol 16:60 (2016).
Myles et al. First-in-human topical microbiome transplantation with Roseomonas mucosa for atopic dermatitis. JCI Insight 3(9):e120608 (2018).
Myles et al. Signaling via the IL-20 receptor inhibits cutaneous production of IL-1 beta and IL-17A to promote infection with methicillin-resistant *Staphylococcus aureus*. Nature Immunol 14(8):804-811 (2013).
Myles et al. *Staphylococcus aureus*: an introduction. Semin Immunopathol 34(2):181-184 (2012).
Myles et al. Transplantation of human skin microbiota in models of atopic dermatitis. JCI Insight 1(10):e86955 (2016).
Myles. Fast food fever: reviewing the impacts of the Western diet on immunity. Nutrition Journal 13:61 (2014).
Nakamura et al. *Staphylococcus* delta-toxin induces allergic skin disease by activating mast cells. Nature 503(7476):397-401 (2013).
Nakatsuji et al. Antimicrobials from human skin commensal bacteria protect against *Staphylococcus aureus* and are deficient in atopic dermatitis. Sci Transl Med 9(378):eaa4680.
Neuber et al. Treatment of atopic eczema with oral mycophenolate mofetil. Br J Dermatol 143(2):385-391 (2000).
Ngugi et al. Effects of Bacterial Vaginosis-Associated Bacteria and Sexual Intercourse on Vaginal Colonization With the Probiotic Lactobacillus crispatus CTV-05. Sex Transm Dis 38(11):1020-1027 (2011).
Nygaard et al. Emerging Treatment Options in Atopic Dermatitis: Systemic Therapies. Dermatology 233:344-357 (2017).
Olle. Medicines from microbiota. Nat Biotechnol 31(4):309-315 (2013).
Pajno et al. Sublingual immunotherapy in mite-sensitized children with atopic dermatitis: a randomized, double-blind, placebo-controlled study. J Allergy Clin Immunol 120(1):164-170 (2007).
Park et al. The Pathogenetic Effect of Natural and Bacterial Toxins on Atopic Dermatitis. Toxins (Basel) 9(1):E3 (19 pgs) (2016).
PCT/US2017/028133 International Search Report and Written Opinion dated Sep. 4, 2017.
Pirie et al. Anemia and iron-restricted erythropoiesis in traumatic critical illness. J Trauma Acute Care Surg 80(3):538-545 (2016).
Proctor et al. Small colony variants: a pathogenic form of bacteria that facilitates persistent and recurrent infections. Microbiology 4:295-305 (2006).
Pullmannová et al. Effects of sphingomyelin/ceramide ratio on the permeability and microstructure of model stratum corneum lipid membranes. Biochimica et Biophysica Acta 1838:2115-2126 (2014).
Pyun, Natural history and risk factors of atopic dermatitis in children. Allergy Asthma Immunol Res 7(2):101-105 (2015).
Reilly. Chapter 80: Pharmaceutical Necessities. Remington: The Science and Practice of Pharmacy, 19th Ed. (Easton, PA: Mack Publishing Co.) (pp. 1380-1404) (1995).
Rietschel et al. Chapter 5: Structure and conformation of the lipid a component of lipopolysaccharides. Handbook of Endotoxin 1:187-214, eds. R. Proctor and E. Rietschel, Elsevier, Amsterdam (1984).

Rosenfeldt et al. Effect of probiotic Lactobacillus strains in children with atopic dermatitis. J Allergy Clin Immunol 111(2):389-395 (2003).
Rudmik et al. Medical Therapies for Adult Chronic Sinusitis: A Systematic Review. JAMA 314(9):926-939 (2015).
Schauber et al. The vitamin D pathway: a new target for control of the skin's immune response? Exp Dermatol 17(8):633-639 (2008).
Schlievert et al. Secreted virulence factor comparison between methicillin-resistant and methicillin-sensitive *Staphylococcus aureus*, and its relevance to atopic dermatitis. J Allergy Clin Immunol 125(1):39-49 (2010).
Shi. The Gut and Skin Microbiome in Atopic Dermatitis. AIHM Annual Conference 2017 (18 pgs) (2017).
Silverberg. Public Health Burden and Epidemiology of Atopic Dermatitis . Dermatol Clin 35:283-289 (2017).
Sipsas et al. Septic arthritis due to Roseomonas mucosa in a rheumatoid arthritis patient receiving infliximab therapy. Diagn Microbiol Infect Dis 55(4):343-345 (2006).
Spanier et al. The associations of triclosan and paraben exposure with allergen sensitization and wheeze in children. Allergy Asthma Proc 35(6):475-481 (2014).
Stevenson et al. Evaluation of matrix-assisted laser desorption ionization-time of flight mass spectrometry for identification of clinically important yeast species. J Clin Microbiol 48:3482-3486 (2010).
Trüper. Etymology in Nomenclature of Procaryotes. Bergey's Manual of Systemic Bacteriology, vol. Two, The Proteobacteria, Part 3, Springer Science & Business Media (pp. 88-99) (2001).
U.S. Appl. No. 15/939,066 Office Action dated Sep. 19, 2018.
U.S. Appl. No. 16/014,971 Office Action dated Sep. 7, 2018.
Wang et al. New insights into T cells and their signature cytokines in atopic dermatitis. IUBMB Life 67(8):601-610 (2015).
Wang et al. Thymic stromal lymphopoietin signaling in CD4(+) T cells is required for TH2 memory. J Allergy Clin Immunol 135:781-791.e3 (2015).
Weston et al. Effects of probiotics on atopic dermatitis: a randomised controlled trial. Arch Dis Child 90(9):892-897 (2005).
Williams et al. The natural history of childhood eczema: observations from the British 1958 birth cohort study. Br J Dermatol 139(5):834-839 (1998).
Wollenberg et al. Current aspects of innate and adaptive immunity in atopic dermatitis. Clin Rev Allergy Immunol 33(1-2):35-44 (2007).
Worth et al. Food allergy and atopic eczema. Clin Rev Allergy Immunol 10(3):226-230 (2010).
Youn et al. Clinical Performance of a Matrix-Assisted Laser Desorption Ionization—Time of Flight Mass Spectrometry Method for Detection of Certain blaKPC-Containing Plasmids. J Clin Microbiol 54(1):35-42 (2015).
Zhang et al. Characterization of the skin fungal microbiota in patients with atopic dermatitis and in healthy subjects. Microbiol Immunol 55:625-632 (2011).
Bieber. Atopic dermatitis. Ann Dermatol. 22:125-37 (2010).
Bieber et al. Pathogenesis of atopic dermatitis: New developments. Curr Allergy Asthma Rep.9:291-4 (2009).
Charman et al. The patient-oriented eczema measure: Development and initial validation of a new tool for measuring atopic eczema severity from the patients' perspective. Arch Dermatol. 140:1513-9 (2004).
Fernandez. Five cases of Pantoea septica related catheter infections. Abstract E0270, presented at 28th ECCMID, Madrid, Spain, Apr. 21-24, 2018 (1 pg.) (2018).
Hanifin et al. Diagnostic features of atopic dermatitis. Acta Derm Venereol. 92:44-7 (1980).
Hanifin et al. The eczema area and severity index (EASI): assessment of reliability in atopic dermatitis. EASI Evaluator Group. Exp Dermatol. 10:11-8 (2001).
Ramakrishnan et al. Skin and Soft Tissue Infections. Am. Fam. Physician. 92(6):474-483 (2015).
Silverberg et al. Association between severe eczema in children and multiple comorbid conditions and increased healthcare utilization. Pediatr Allergy Immunol. 24:476-86 (2013).

(56) References Cited

OTHER PUBLICATIONS

Tan et al. Pathogenicity of Moraxella osloensis, a Bacterium Associated with the Nematode Phasmarhabditis hermaphrodita, to the Slug Deroceras reticulatum. Applied and Environmental Microbiology 67(11):5010-5016 (2001).
U.S. Appl. No. 16/184,498 Office Action dated May 15, 2019.
U.S. Appl. No. 16/271,577 Office Action dated May 9, 2019.
U.S. Appl. No. 16/288,360 Office Action dated May 30, 2019.
Williams et al. Is eczema really on the increase worldwide? J Allergy Clin Immunol. 121:947-54.e15 (2008).
Zuberbier et al. Patient perspectives on the management of atopic dermatitis. J Allergy Clin Immunol. 118:226-32 (2006).
U.S. Appl. No. 16/271,552 Office Action dated Mar. 18, 2019.
Co-pending U.S. Appl. No. 16/386,736, filed Apr. 17, 2019.
Co-pending U.S. Appl. No. 16/401,986, filed May 2, 2019.
Co-pending U.S. Appl. No. 16/522,333, filed Jul. 25, 2019.
Co-pending U.S. Appl. No. 16/522,357, filed Jul. 25, 2019.
Co-pending U.S. Appl. No. 16/522,379, filed Jul. 25, 2019.
PCT/US2018/059073 International Search Report and Written Opinion dated Feb. 15, 2019.
PCT/US2019/027912 International Search Report and Written Opinion dated Jul. 17, 2019.
PCT/US2019/030444 International Search Report and Written Opinion dated Aug. 30, 2019.
PCT/US2019/030444 Invitation to Pay Additional Fees dated Jul. 5, 2019.
U.S. Appl. No. 16/271,552 Office Action dated Aug. 23, 2019.
Mankowska-Wierzbicka et al. The Microbiome and Dermatological Diseases. Postepy Hig Med Dosw 69:978-985 (2015).
U.S. Appl. No. 16/386,736 Office Action dated Feb. 12, 2020.
Jewelewicz et al. Modified rapid deployment hemostat bandage reduces blood loss and mortality in coagulopathic pigs with severe liver injury. J Trauma 55:275-281 (2003).
Kim et al.: Two Cases of Bacteremia Due to Roseomonas Mucosa. Annals of Laboratory Medicine 36: 367-370 (2016).
Romano-Bertrand et al.: Skin Microbiota is the Main Reservoir of Roseomonas Mucosa, an Emerging Opportunistic Pathogen so Far Assumed to be Environmental. Clinical Microbiology and Infection 22: 737e1-737e7 (2016).
Truant et al. Methylobacterium Species: An Increasingly Important Opportunistic Pathogen. Laboratory Medicine 29(11):704-710 (1998).
U.S. Appl. No. 16/184,498 Office Action dated Oct. 11, 2019.
U.S. Appl. No. 16/244,903 Office Action dated Dec. 4, 2019.
U.S. Appl. No. 16/244,903 Office Action dated Sep. 9, 2019.
U.S. Appl. No. 16/271,577 Office Action dated Oct. 11, 2019.
U.S. Appl. No. 16/288,630 Office Action dated Oct. 11, 2019.
U.S. Appl. No. 16/522,333 Office Action dated Nov. 5, 2019.
U.S. Appl. No. 16/522,357 Office Action dated Oct. 17, 2019.
U.S. Appl. No. 16/522,379 Office Action dated Jan. 9, 2020.
U.S. Appl. No. 16/522,379 Office Action dated Oct. 28, 2019.

\* cited by examiner

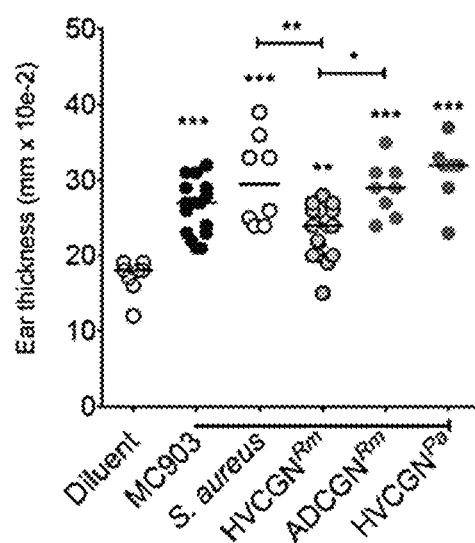
FIG. 3A
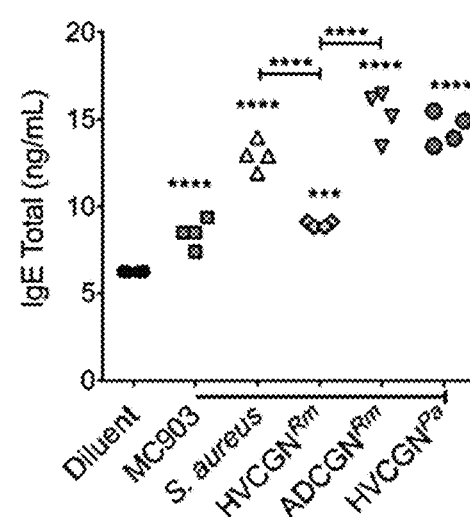
FIG. 3B
FIG. 3C
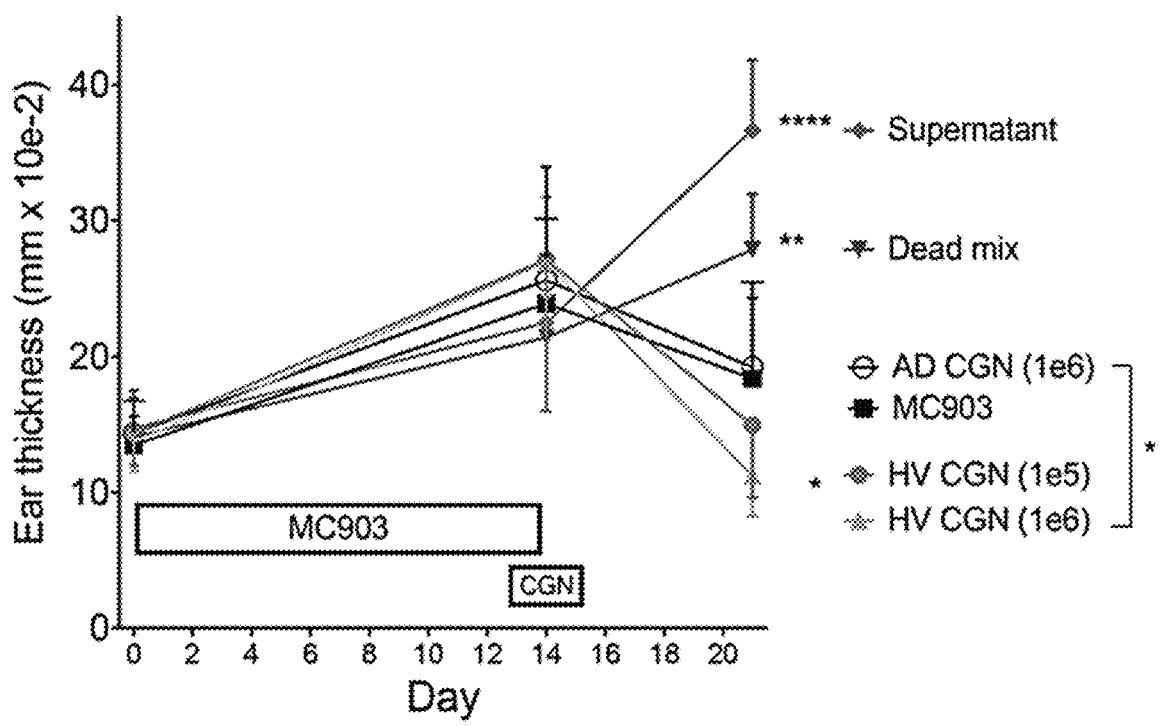

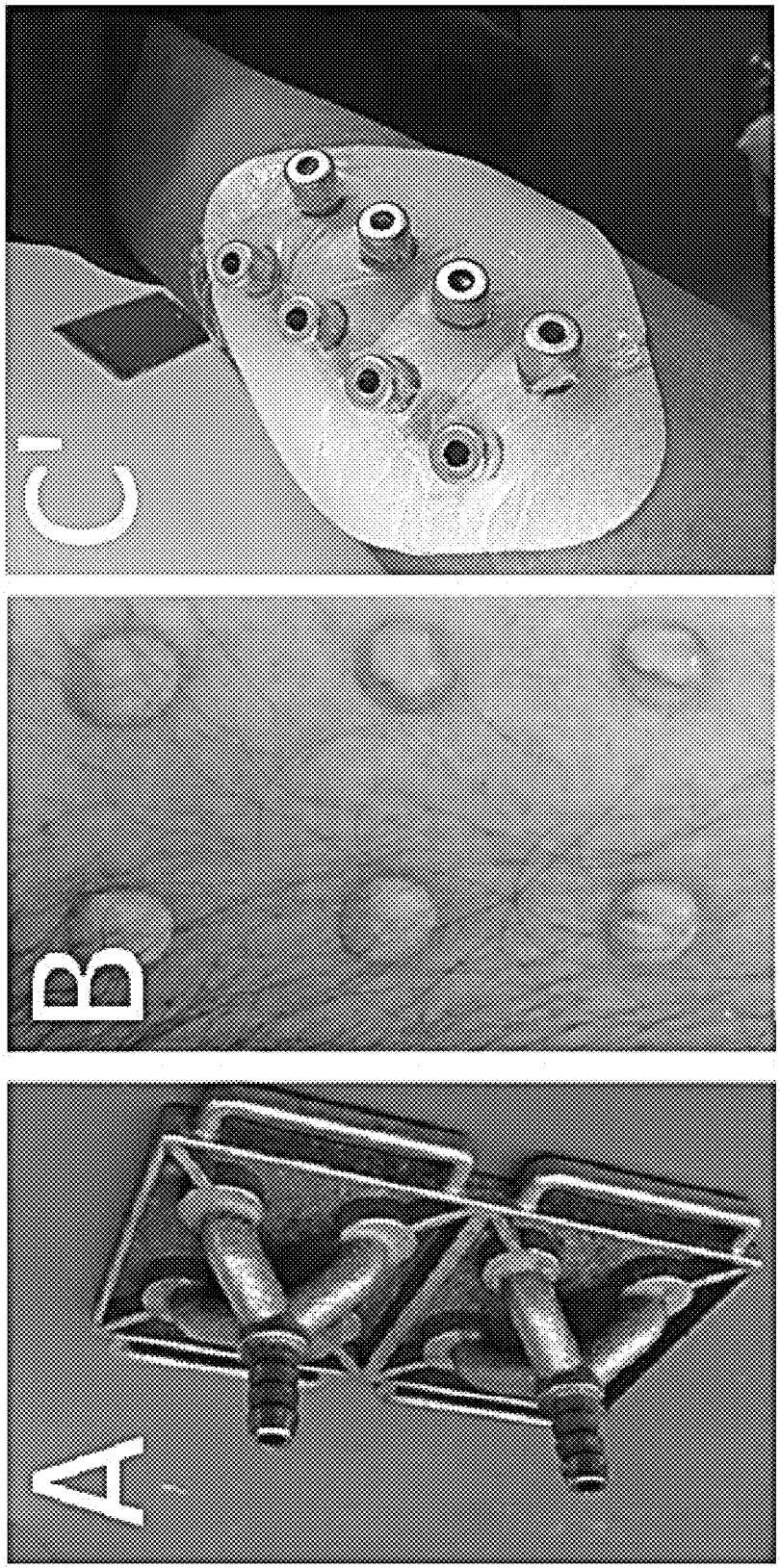

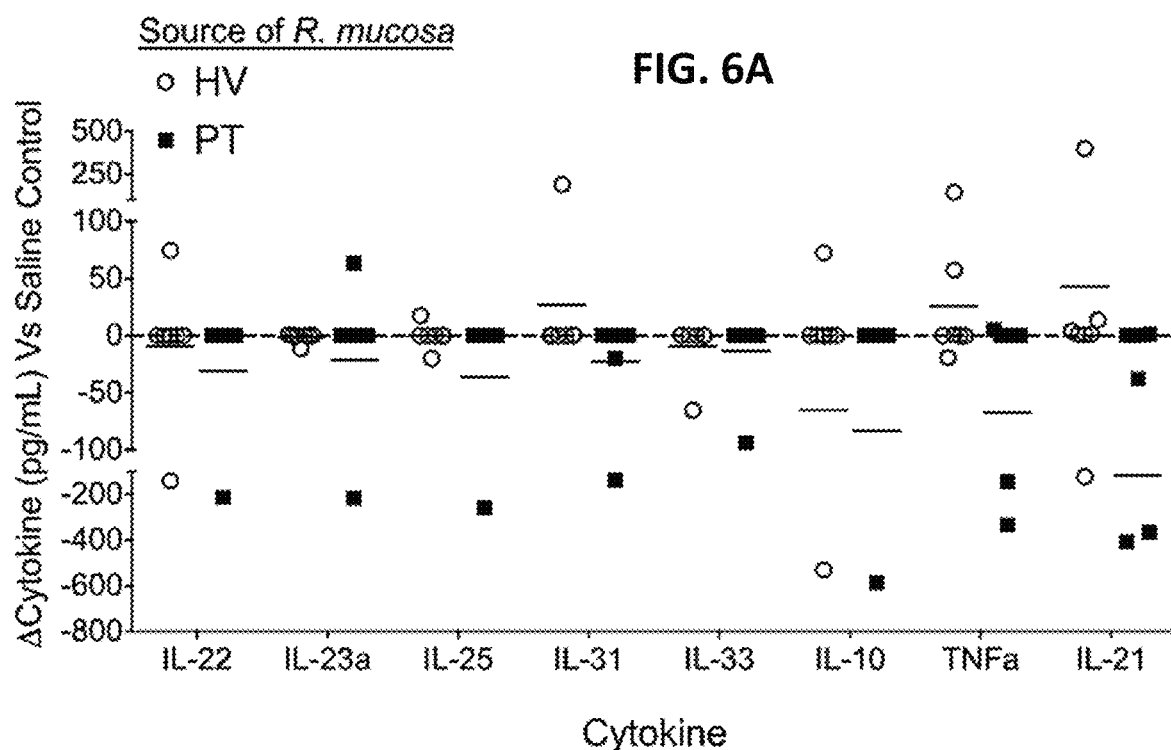
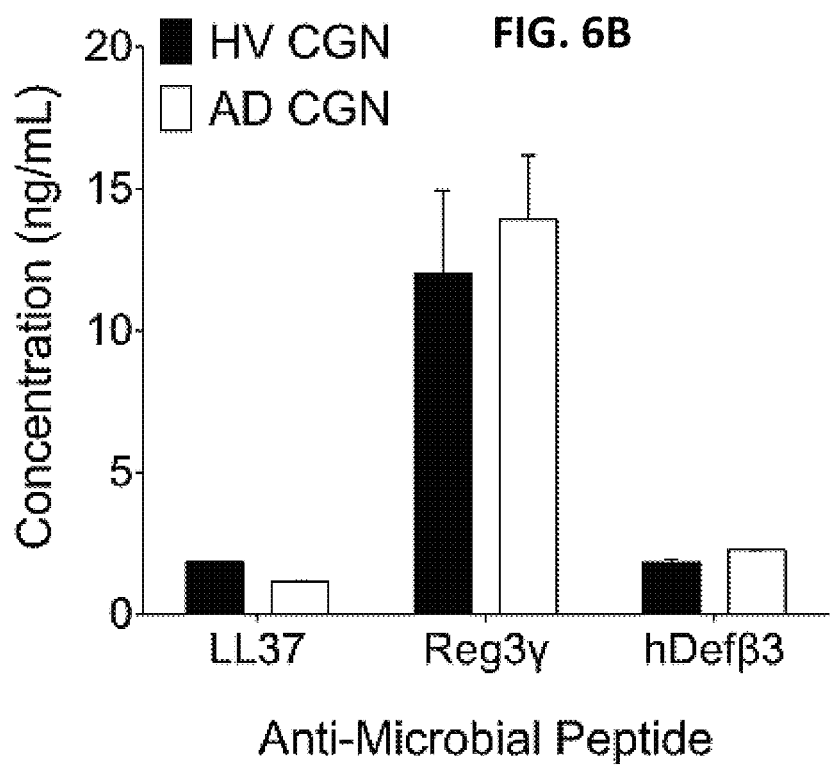

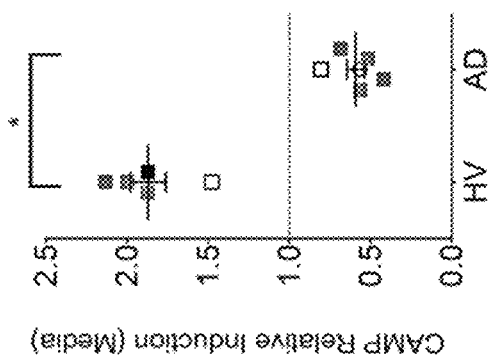
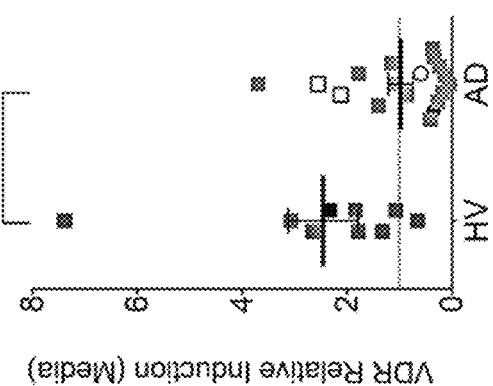
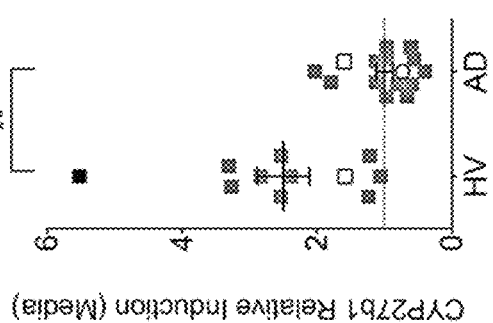
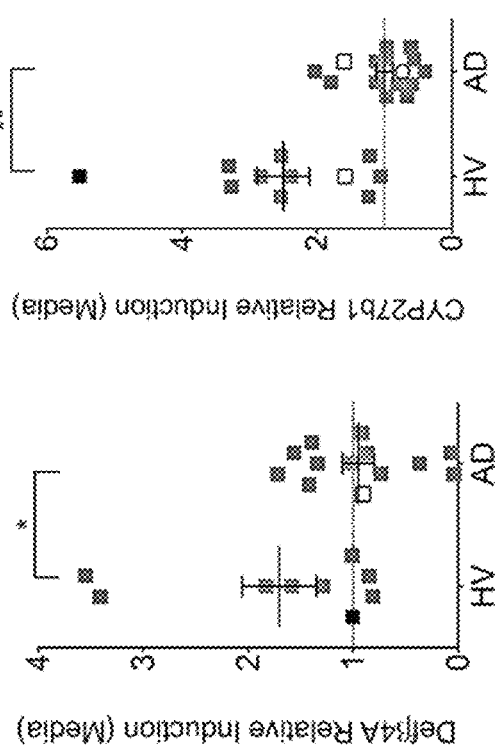

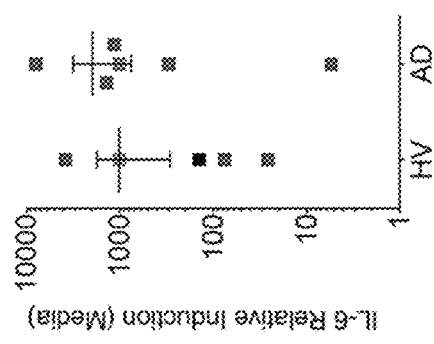
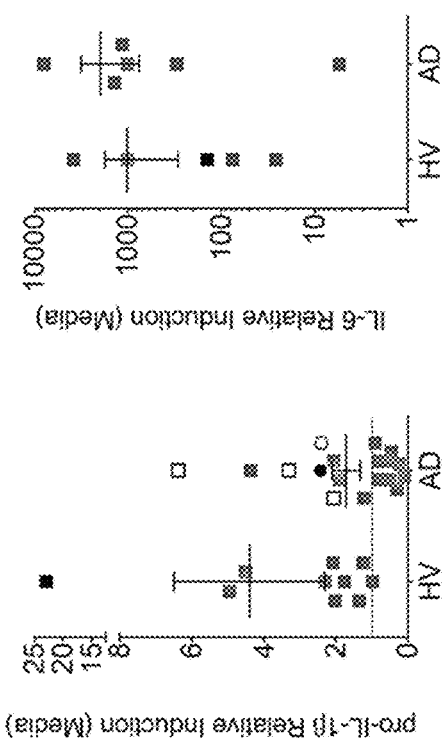
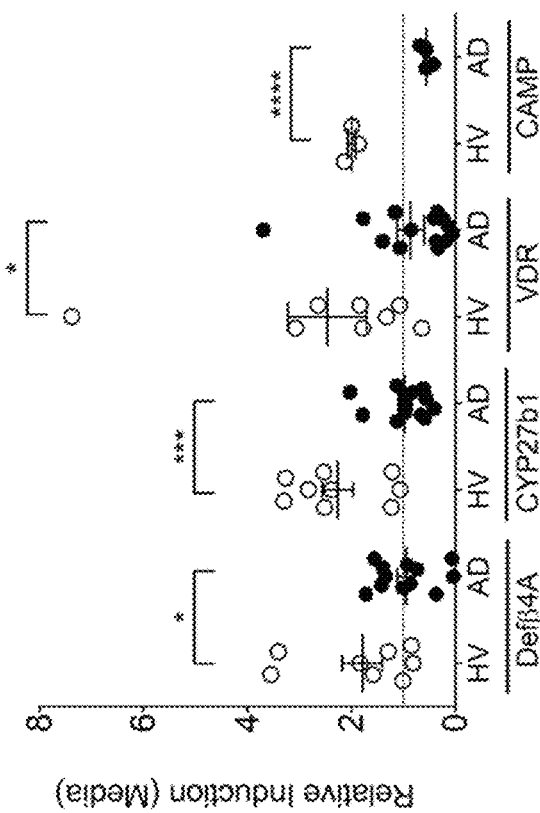

USE OF GRAM NEGATIVE SPECIES TO TREAT ATOPIC DERMATITIS

CROSS REFERENCE TO RELATED APPLICATION

This application is a continuation of U.S. application Ser. No. 16/014,971, filed Jun. 21, 2018, now U.S. Pat. No. 10,206,957, issued on Feb. 19, 2019, which is a Divisional of U.S. application Ser. No. 15/939,066, filed Mar. 28, 2018, now U.S. Pat. No. 10,195,236, issued on Feb. 5, 2019, which is a continuation of PCT International No. PCT/US2017/028133, filed Apr. 18, 2017, which claims the benefit of U.S. Provisional Application No. 62/324,762, filed Apr. 19, 2016, each of which is hereby incorporated by reference in its entirety.

FIELD OF THE DISCLOSURE

This disclosure relates to the field of dermatology, specifically to the use of the topical application of viable gram negative bacterial to treat atopic dermatitis.

BACKGROUND

The term "eczema," often used to describe atopic dermatitis, was coined in ancient Greece, and roughly translates as "to boil out." Modern science, however, recognizes the contribution of both host and environmental factors to this disease. Hallmarks of the disease include reduced barrier function, reduced innate immune activation, and susceptibility to infections with *Staphylococcus aureus*. Predisposing host factors are suggested by monogenic mutations in STAT3, filaggrin, and other genes associated with AD-like phenotypes (Lyons et al., *Immumology and allergy clinics of North America* 35, 161-183 (2015); published online Epub February (10.1016/j.iac.2014.09.008)). Host genetic influences can be therapeutically modulated through topical steroids or calcineurin inhibitors (Boguniewicz and Leung, *J Allergy Clin Immunol* 132, 511-512 e515 (2013); published online (Epub) August (10.1016/j.jaci.2013.06.030)). *S. aureus* contributes to AD pathogenesis, and can be mitigated by antibiotics (Boguniewicz and Leung, supra; Kobayashi et al., *Immunity* 42, 756-766). Recent work has revealed that the skin microbiome is significantly different between healthy controls and patients with AD and that symptoms are associated with a loss of commensal diversity (Kong et al., *Genome research* 22, 850-859 (2012); published online (Epub) May (10.1101/gr.131029.111)). A need remains for methods for therapeutically targeting this dysbiosis and treating atopic dermatitis.

SUMMARY OF THE DISCLOSURE

It is disclosed herein that culturable gram negative bacteria (CGN) from the skin of healthy subjects were associated with activation of innate immunity, enhanced barrier function, and control of *S. aureus*. These gram negative bacteria are of use for treating atopic dermatitis in subjects with this condition.

In some embodiments, pharmaceutical compositions are disclosed that include a therapeutically effective amount of a purified viable gram negative bacteria and a pharmaceutically acceptable carrier, wherein a) a lysate and/or component of the gram negative bacteria inhibits growth of *S. aureus* in an in vitro assay; b) the gram negative bacteria stimulates human keratinocytes; c) the gram negative bacteria induces cytokine expression from human cells; and d) the gram negative bacteria is non-pathogenic when administered to the skin of the subject. The pharmaceutical compositions are formulated for topical administration.

Methods of treating a topical dermatitis using these pharmaceutical compositions are also disclosed.

The foregoing and other features and advantages of the invention will become more apparent from the following detailed description of several embodiments which proceeds with reference to the accompanying figures.

BRIEF DESCRIPTION OF THE FIGURES

FIGS. 3A-3D: CGN from HV improves outcomes in the MC903 mouse model of AD-like dermatitis. (A-B) Both ears of mice were inoculated daily with *R. mucosa* (Rm) from a HV or an AD patient, or *P. aeruginosa* (Pa) from a HV, or SAAS9 strain of *S. aureus* for 2 days prior to MC903 application. Then bacteria were co-applied with MC903 daily for 13 days. Day 14 ear thickness (A) for each ear and serum total IgE levels (B) are shown; N=4-8 mice per group. (C-D) Mice were treated with MC903 for 14 days to induce AD-like dermatitis. Starting on day 13, mice were treated daily for 3 day with 1e6 CFU of live *R. mucosa* from a HV or AD patient (HVCGN and ADCGN), 1e6 CFU of killed *R. mucosa* from the same HV re-suspended in the supernatant from 3e6 CFU of autologous *R. mucosa* (Dead mix), or supernatant from 1e7 CFU of the HV *R. mucosa* (Sup). Day 21 visual redness (D) and ear thickness (C) are shown; N=3-5 mice per group. Data shown are representative of three independent experiments and displayed as mean+sem. Significance determined by ANOVA.

FIGS. 5A-5C: Suction Blister Protocol. (A) Image of 3D printed blister induction device. (B) Blister results 2 hours after suction. (C) Challenge chamber placed over denuded blister areas, bacterial isolates placed via pipette into the center of each challenge cap.

FIGS. 6A-6B: CGN Impacts on cytokine and antimicrobial peptide responses. Cytokine analysis (A) and antimicrobial peptides (B) for in vivo human blister challenge (see supplemental methods), N=5. Data shown are a combination of five independent experiments and displayed as mean+sem (B) or mean and individual participants (A).

FIGS. 7A-7G: CGN stimulate primary human keratinocytes. Primary human foreskin keratinocytes were cultured to confluence. 1e7 CFU of gram negative bacteria were added per well. mRNA was harvested from the KC 24 hours later and analyzed by PCR Data is representative of three independent experiments and displayed as mean+sem with individual dots representing KC cultured with distinct isolates. Significance determined by Student t-test $*=p<0.05$. $**=p>0.01$.

DETAILED DESCRIPTION OF SEVERAL EMBODIMENTS

Figure 1A:
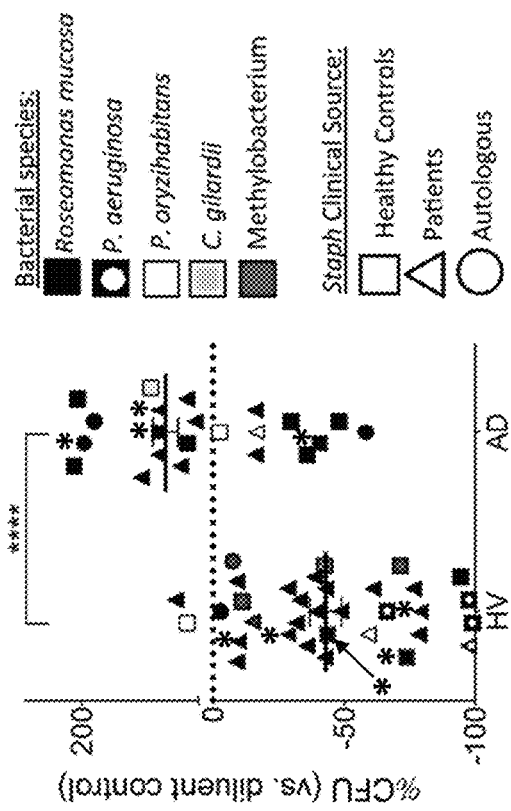
FIGS. 1A-1D: CGN isolates differ in presence and *S. aureus* inhibition between healthy volunteers and patients with AD. (A) Percentage of individuals with CGN isolate yield from HV (n=26) and AD (n=17) subjects. Individuals with multiple CGN isolates were counted per isolate for >100% total in HV; see Table 1 for details. (B) Eight strains of *S. aureus* isolated from HV and AD patients were grown in the presence of either CGN supernatant or control media. Each data point represents the effect on *S. aureus* growth of supernatant from one CGN isolate compared to media control (HV isolates=9, AD isolates=7); shapes represent sourcing of *S. aureus* as either the participant's autologous *S. aureus*, or one *S. aureus* isolate from HV or AD patients. Data points with a * symbol represent one HV- and one AD-derived CGN isolate selected for subsequent human challenge and mouse model experiments. Data is alternatively presented by CGN species, see FIG. 4. (C) Healthy mouse ears were co-inoculated with *S. aureus* (strain SAAS9) and *R. mucosa* (Rm) from HV or AD patients, or *P. aeruginosa* from a HV for 10 days. Day 12 ears were homogenized and plated by serial dilution for CFU. Percent change in growth versus diluent (no CGN added) control is shown. (D) CGN CFU yield taken from same mice as panel C. Data shown are a combination of three or more independent experiments (B) or representative of two independent experiments (C-D) and displayed as mean+sem. SA=*S. aureus*, HV=Healthy Volunteer, AD=Atopic Dermatitis, CGN=Culturable gram negative, Rm=*Roseomonas mucosa*. Pa=*Pseudomonas aeruginosa*. Significance determined by Student's t test (B) or ANOVA with Bonferroni's correction (C-D).

It is disclosed herein that commensal organisms from healthy controls differ in their immune activation, barrier function, and antimicrobial profiles when compared to identical species taken from patients with atopic dermatitis. Thus, a live-biotherapeutic approach to treating patients with atopic dermatitis is provided.

Pharmaceutical compositions, formulated for topical administration, are disclosed herein which can be used for the treatment of atopic dermatitis. These pharmaceutical compositions include a therapeutically effective amount of a purified viable gram negative bacteria and a pharmaceutically acceptable carrier, wherein a) a lysate and/or component of the gram negative bacteria inhibits growth of *S. aureus* in an in vitro assay; b) the gram negative bacteria stimulates human keratinocytes; c) the gram negative bacteria induces cytokine expression from human cells; and d) the gram negative bacteria is non-pathogenic when administered to the skin of the subject. In a specific non-limiting example, the gram negative bacteria produce lysophosphatidylcholine.

The gram negative bacteria can be from any species. Thus, in certain examples, if the gram negative bacteria is *Pseudomonas*, the gram negative bacterium can be a *Pseudomonas aeruginosa*. *Pseudomonas luteola*, or *Pseudomonas orbyhabitans*. In other examples, if the gram negative bacterium is *Pantoea*, the gram negative bacterium can be *Pantoea septica*. In additional examples, if the gram negative bacterium is *Moraxella*, the gram negative bacterium can be *Moraxella osloensis*. In further examples the gram negative bacterium is *Roseomonas*, the gram negative bacterium can be *Roseomonas mucosa*. The gram negative bacteria included in the pharmaceutical composition can be from a single strain, a single species, or a single Genus. Alternatively, combinations of strains, species and/or genera of gram negative bacteria can be used in the disclosed methods.

Terms

Definitions of common terms in molecular biology may be found in Benjamin Lewin, *Genes V*, published by Oxford University Press, 1994 (ISBN 0-19-854287-9); Kendrew et al. (eds.). *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers. Inc., 1995 (ISBN 1-56081-569-8).

In order to facilitate review of the various embodiments of this disclosure, the following explanations of specific terms are provided:

Atopic dermatitis: A chronic disease that affects the skin. In atopic dermatitis, the skin becomes extremely itchy. Scratching leads to redness, swelling, cracking, "weeping" clear fluid, and finally, crusting and scaling. In most cases, there are periods of exacerbations followed by periods of remissions. Although it is difficult to identify exactly how many people are affected by atopic dermatitis, an estimated 20% of infants and young children experience symptoms of the disease. Approximately 60% of these infants continue to have one or more symptoms of atopic dermatitis in adulthood. Thus, more than 15 million people in the United States have symptoms of the disease. The "lesion area" is the region of the skin affected by atopic dermatitis. Generally a lesion is characterized by skin dryness (xerosis), redness, blisters, scabs, or any combination. A non-lesion area is not affected by atopic dermatitis or any other skin pathology.

Animal: Living multi-cellular vertebrate organisms, a category that includes, for example, mammals and birds. The term mammal includes both human and non-human mammals. Similarly, the term "subject" includes both human and veterinary subjects.

Antibiotic: A compound or substance that kills or substantially slows down the growth of bacteria, fungus or any other microbe. An "antibacterial" is a compound or substance that kills or substantially slows the growth of bacteria.

Antibacterial antibiotics are commonly classified based on their mechanism of action, chemical structure, or spectrum of activity. Most target bacterial functions or growth processes. Those that target the bacterial cell wall (for example, penicillins and cephalosporins) or the cell membrane (for example, polymixins), or interfere with essential bacterial enzymes (for example, quinolones and sulfonamides) are bactericidal. Those that target protein synthesis (for example, aminoglycosides, macrolides, and tetracyclines) are generally bacteriostatic. Further categorization is based on their target specificity.

"Narrow-spectrum" antibacterial antibiotics target specific types of bacteria, such as gram negative or gram positive bacteria. "Broad-spectrum antibiotics" affect a number of different types of bacteria. Antibacterial agents also include cyclic lipopeptides (such as daptomycin), glycylcyclines (such as tigecycline), and oxazolidinones (such as linezolid).

Topical antibiotics are antibiotics that are applied to a body surface, such as the skin or eye. Topical antibiotics are often formulated in an ointment or a cream, and contain active agents such as macrolide antibiotic (such as erythromycin), a sulfa antibiotic (such as sulfacetamide), a cyclic peptide (such as bacitracin a polymyxin) a psuedomonic acid (such as mupirocin), an ammyroglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Commensal: Organisms are commensal when they can live in the same environment and one benefits from another without affecting (either harming or benefitting) the other. Bacteria in the skin microbiota are considered to be commensal with the host, such as a human. The number of commensal bacterial species present in skin microbiota can be detected, for example, using 16S ribosomal RNA to identify bacterial species present.

Epithelial Cell: A closely packed cell that forms an epithelium, such as in the skin. There are several types of epithelium, including simple squamous epithelium, simple cuboidal epithelium, simple columnar epithelium, pseudostratified columnar epithelium, stratified squamous (nonkeratinized) epithelium, stratified cuboidal epithelium, and transitional epithelium.

Gram Negative Bacteria: Those bacteria having a plurality of exterior membranes, an inner cell membrane, a thin peptidoglycan layer, and an outer membrane containing lipopolysaccharides (LPS). Porins exist in the outer membrane and the gram negative bacteria do not retain the crystal violet stain in the Gram staining method of bacterial differentiation. Between the outer membrane and the cytoplasmic member there is space filled with periplasm. A S-layer is directly attached to the outer membrane. Teichoic acids or lipoteichoic acids are not present. Most gram negative bacteria, (but not all) do not form spores. Typical gram negative species include but are not limited to those most commonly associated with sepsis and septic shock in humans, e.g., as reported in the HANDBOOK OF ENDOTOXINS, 1: 187-214, eds. R. Proctor and E. Rietschel, Elsevier, Amsterdam (1984). A conserved signature indel (CSI) in the HSP60 (GroEL) protein distinguishes all traditional phyla of gram negative bacteria (e.g., *Proteobacteria, Aquificae, Chlamydiae, Bacteroidetes, Chlorobi, Cyanobacteria, Fibrobacteres, Verrucomicrobia, Planctomycetes, Spirochetes,* and *Acidobacteria*). Gram negative bacterial include, but are not limited to, *Escherichia coli, Klebsiella pneumoniae, Proteus* species, *Pseudomonas, Salmonella,* and *Rosemononas* species. CGN are the gram negative bacterial found in the skin. By "component" is meant any molecule present in, or secreted by, the gram negative bacteria. Thus, a component can be present in a lysate or a supernatant. In specific non-limiting examples, a component of a gram negative bacteria, such as included in a supernatant, inhibits growth of *S. aureus* in an in vitro assay.

Gram Positive Bacteria: Bacteria that retain the crystal violet stain in the Gram staining method of bacterial differentiation. These bacteria are characterized by a preponderance of peptidoglycans relative to LPS molecules in their membranes, which are capable of inducing disease etiology and symptoms characteristic of microbe infection, similar to those described for gram negative species.

Heterologous: Originating from separate genetic sources or species. A polypeptide that is heterologous is derived from a different cell or tissue type, or a different species from the recipient, and is cloned into a cell that normally does not express that polypeptide.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Microbiome: The genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as micro RNA and ribosomal RNA, the epigenome, plasmids, and all other types of genetic information.

Immunocompetent: A subject, such as a human, that does not have an immune deficiency, such as a humoral (B cell) immune deficiency, a T cell deficiency, or a complement deficiency. An immunocompetent subject can mount an immune response to a bacterial infection. "Immunocompetence" is the ability of the body to produce a normal immune response following exposure to an antigen or a bacteria.

Isolated or Purified: An "isolated" or "purified" cell, such as gram negative bacteria, has been separated or purified away from other cells or species in the environment which the cell, such as the bacteria occurs. The term "isolated" thus encompasses a bacterium purified by standard purification methods, such as single cell cloning and culture. The term also embraces a bacterium prepared by recombinant methods or isolated from a natural source. Isolated (or purified) gram negative bacteria are generally removed from other bacteria, such as gram positive bacteria. Isolated gram negative bacteria can be of a single genus, species, and/or strain. The term "substantially purified" as used herein refers to a bacterial genus, species strain or a mixture of more than one bacterial strains (e.g. gram negative bacteria) that are substantially enriched in a sample, such that other types of bacteria (e.g., gram positive bacteria) are depleted. The sample can be substantially purified or enriched for the bacterial strain or mixture of strains of interest such that the sample is at least about 70%, 80%, 85%, 90%, 95%, 99% or greater of the desired bacterial genus species, strain(s) or less than about 30%, 20%, 15%, 14%, 13%, 12%, 11%, 10%, 9%, 8%, 7%, 6%, 5%, 4%, 3%, 2%, 1% or less of the undesirable or other bacterial genus, species or strains.

Inhibiting or treating a disease: Inhibiting a disease, such as atopic dermatitis, refers to inhibiting the full development of a disease. In several examples, inhibiting a disease refers to lessening symptoms or a decrease in lesion size. "Treatment" refers to a therapeutic intervention that ameliorates a sign or symptom of a disease, such as redness, swelling, cracking. "weeping" clear fluid, and finally, crusting and scaling of the skin.

Interleukin (IL)-6. An IL that acts as both a pro-inflammatory cytokine and an anti-inflammatory myokine. IL-6 signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardiotrophin-1, and is almost ubiquitously expressed in most tissues. In contrast, the expression of CD126 is restricted to certain tissues. As IL-6 interacts with its receptor, it triggers the gp130 and IL-6R proteins to form a complex, thus activating the receptor. Exemplary amino acid sequences are provided in Uniprot database Accession No. P05231 (human) and P08505 (mouse) and exemplary mRNA sequences encoding IL-6 (along with the corresponding protein sequence) are provided in GENBANK® Accession Nos. NM_000600.4 (human), Jan. 5, 2016, and NM_031168.2 (mouse), Oct. 26, 2015, which are all incorporated by reference herein.

Mammal: This term includes both human and non-human mammals. Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Pharmaceutical agent: A bacteria, such as a gram negative bacteria, chemical compound, nucleic acid molecule, or composition capable of inducing a desired therapeutic or prophylactic effect when properly administered to a subject. In one embodiment, a pharmaceutical agent is a gram negative bacterium.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of a gram negative bacteria herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. Acceptable carriers also include creams and ointments, such as for topical administration.

*Pseudomonas*: A genus of gram negative, aerobic gammaproteobacteria, belonging to the family Pseudomonadaceae containing 191 described species. The members of the genus demonstrate a great deal of metabolic diversity, and consequently are able to colonize a wide range of niches. Members of this genus can be determined using 16S rRNA analysis. Generally, members of the genus are rod shaped, aerobic, non-spore forming bacteria that have one or more polar flagella, and exhibit positive oxidase and catalase tests.

*Roseomonas*: A genus of aerobic, gram negative, rod shaped bacterium assigned to the phylum Proteobacteria and the family Acetobacteraceae. In specific non-limiting examples, bacteria can be determined to be in the genus *Roseomonas* by evaluating the nucleic acid sequence of 16S rRNA from the bacteria. *Roseomonas* can appear as plump cocci, coccobacilli, or short rods, depending on the species. Most strains grow on MacConkey agar, and growth occurs at 25° C., 30° C. and 35° C., and temperatures in between. Most strains also grow at 42° C. A pale pink growth pigment is produced, see BERGEY'S MANUAL® of Systemic Bacteriology. Volume Two. The Proteobaceria. Part 3, Springer Science & Business Media, July 25, 206, pages 88-89, available on-line from Google books.

Therapeutically effective dose: A dose sufficient to treat atopic dermatitis. In one embodiment, a therapeutically effective dose is an amount of a gram negative bacteria sufficient to reduced lesion size.

Topical application: A topically applied agent is applied only in a specific area, and not throughout the body. In particular examples the composition is applied to the skin, such as in a lesion. For example the pharmaceutical composition can be applied in a pharmaceutical preparation to a lesion.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in gram negative bacteria.

Unless otherwise explained, all technical and scientific terms used herein have the same meaning as commonly understood by one of ordinary skill in the art to which this disclosure belongs. The singular terms "a," "an." and "the"

include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Gram Negative Bacteria

Provided are pharmaceutical compositions that include isolated or substantially purified gram negative bacteria and combinations of gram negative bacteria from intact human skin, or propagated from such gram negative bacteria. These gram negative bacteria have the capacity to meaningfully provide functions of a healthy microbiota or catalyze an augmentation to the resident microbiome when administered to a subject with atopic dermatitis. In particular, compositions are provided that treat, prevent, delay or reduce the symptoms of atopic dermatitis.

These compositions can include gram negative bacteria isolated from a subject that does not have atopic dermatitis, such as a healthy subject without any pathological condition of the skin. In some embodiments, the subject does not have any pathological condition, for example, a pathological condition of the skin and/or any internal organ. The subject can be immunocompetent. The gram negative bacteria can be isolated from the skin of the subject directly, or can be propagated in vitro using standard techniques for culturing bacteria. However, the gram negative bacteria can be obtained from other sources, as discussed below. The gram negative bacteria can be *Proteobacteria, Spirochaetaceae, Enterobacteriales, Fusobacterium polymorphum,* or a *Selenomaonadales*. The gram negative bacteria can be diplococci, coccobacilli, cocci or a bacilli.

In some embodiments, disclosed are compositions formulated for topical administration that include an isolated or substantially purified viable gram negative bacteria and a pharmaceutically acceptable carrier, wherein a) a lysate and/or component of the gram negative bacteria inhibits growth of *S. aureus* in an in vitro assay; b) the gram negative bacteria stimulates human keratinocytes; c) the gram negative bacteria induces cytokine expression from human cells; and d) the gram negative bacteria is non-pathogenic when administered to the skin of an immunocompetent subject. By "component" is meant any molecule present in, or secreted by, the gram negative bacteria. In specific non-limiting examples, a supernatant, which includes molecules secreted by the gram negative bacteria, inhibits growth of *S. aureus* in an in vitro assay.

Provided herein are specific genera, species, strains, and combinations of strains or species, originally found within the human skin microbiota of a subject without atopic dermatitis, such as a healthy subject.

In some embodiments, these species/strains are able to significantly reduce the rate of skin pathogen replication within the in vitro assay. These species/strains are capable of providing a safe and effective means by which to affect the growth, replication, and disease severity of such bacterial pathogens. In some embodiments, bacterial compositions are provided with the ability to exclude pathogenic bacteria.

Exemplary bacterial compositions are demonstrated to reduce the growth rate of a specific pathogen, such as *S. aureus*. A gram negative bacteria with the capacity to durably reduce *S. aureus* in the skin can be identified using a methodology for estimating an Ecological Control Factor (ECF) for constituents within the human microbiota. The ECF is determined by assessing the antagonistic activity of a given commensal strain or combination of strains towards a given pathogen (e.g., *S. aureus*) using an in vitro assay, resulting in observed levels of ecological control at various concentrations of the added commensal strains. The ECF for a commensal strain or combination of strains is somewhat analogous to the longstanding minimal inhibitory concentration (MIC) assessment that is employed in the assessment of antibiotics. The ECF allows for the assessment and ranking of relative potencies of commensal strains and combinations of strains for their ability to antagonize skin pathogens. The ECF of a commensal strain or combination of strains can be calculated by assessing the concentration of that composition that is able to mediate a given percentage of inhibition (e.g., at least 10%, 20%, 50%, 70%, 75%, 80%, 85%, 90%, 95%, or 100%) of a target pathogen (e.g., *S. aureus*) in the in vitro assay.

In some embodiments, the gram negative bacteria stimulates human keratinocytes. The gram negative bacteria can stimulate keratinocytes in vivo and/or in vitro. Gram negative bacteria stimulate keratinocytes by increasing the transcription of the mRNA of immune mediators or molecules involved in epithelial barrier function, such as production of an mRNA encoding IL-1β, an mRNA encoding defensin beta 4, an mRNA encoding Cyp27b1, an mRNA encoding a vitamin D receptor, an mRNA encoding occludin, an mRNA enocoding claudin 1, and/or an mRNA encoding fillagrin.

In additional embodiments, the gram negative bacteria induces cytokine expression from human cells. Human cells include, but are not limited to, the cells of the skin such as fibroblasts and keratinocytes. Cytokines include, but are not limited to, an interleukin (IL) such as IL-6 and IL-1β.

In yet other embodiments, the gram negative bacteria produce lysophosphatidylcholine.

In further embodiments, the gram negative bacteria is non-pathogenic when administered to the skin of the subject such as in a immunocompetent subject. Generally, the gram negative bacteria does not cause any infection when administered to intact human skin. Thus, no pathogenesis is observed following treatment.

The viable gram negative bacteria included in the disclosed composition can be of any genus. In some embodiments, the gram negative bacteria is *Pseudomonas*. In additional embodiments, the gram negative bacteria is *Pantoea* or a *Moraxella*. In other embodiments, the gram negative bacteria is *Roseomonas*.

Bacteria from only a single genus can be included in the pharmaceutical composition. Alternatively, combinations of genera can be included in a pharmaceutical composition and are of use in the disclosed methods. Thus, the composition can include, for example, 1, 2, 3, 4, or 5 genera of gram negative bacteria. In one specific non-limiting example, the composition includes viable *Roseomonas*. In another specific non-limiting example, the compositions includes viable *Pseudomonas*. In yet another specific non-limiting example, the compositions includes viable *Roseomonas and* viable *Pseudomonas*.

The viable gram negative bacteria can be from any species. Thus, in certain examples, if the gram negative bacteria is Pseudomonas, the gram negative bacterium can be a Pseudomonas aeruginosa, Pseudomonas luteola, or Pseudomonas orbyhabitans. In other examples, if the gram negative bacterium is Pantoea, the gram negative bacterium can be Pantoea septica. In additional examples, if the gram negative bacterium is Moraxella, the gram negative bacterium can be Moraxella osloensis. In further examples the gram negative bacterium is Roseomonas, the gram negative bacterium can be Roseomonas aerilata, Roseomonas aerophila, Roseomonas aestuarii, Roseomonas alkaliterrae, Roseomonas aquatic, Roseomonas cervicalis, Roseomonas fauriae, Roseomonas frigidaquae, Roseomonas gilardii, Roseomonas lacus, Roseomonas ludipueritiae, Roseomonas mucosa, Roseomonas pecuniae, Roseomonas rhizosphaerae, Roseomonas riguiloci, Roseomonas rosea, Roseomonas soli, Roseomonas stagni, Roseonmonas terrae, or Roseomonas vinacea. In one specific non-limiting example, the gram negative bacteria is Roseomonas mucosa.

Gram negative bacteria of a single species can be include in the pharmaceutical composition. Alternatively, combinations of species gram negative bacteria can be included in a pharmaceutical composition are of use in the disclosed methods. Thus, the composition can include 1, 2, 3, 4, or 5 species of gram negative bacteria. In one specific non-limiting example, the composition includes viable Roseomonas mucosa. In another specific non-limiting example, the compositions includes viable Pseudomonas aeruginosa. In yet another specific non-limiting example, the compositions includes viable Roseomonas mucosa and viable Pseudomonas aeruginosa.

The viable gram negative bacterium of use can be from a single strain. Alternatively, the gram negative bacteria can be from multiple strains. Gram negative bacteria of a single strain, or combinations of strains gram negative bacteria can be included in the disclosed compositions are of use in the disclosed methods. Thus, the composition can include 1, 2, 3, 4, or 5 species of gram negative bacteria. In one specific non-limiting example, the composition includes a single strain of viable Roseomonas mucosa. In a further specific non-limiting example, the composition includes 2, 3, 4, or 5 strains of viable Roseomonas mucosa. In another specific non-limiting example, the composition includes a single strain of viable Pseudomonas aeruginosa. In a further specific non-limiting example, the composition includes 2, 3, 4, or 5 strains of viable Pseudomonas aeruginosa. In yet another specific non-limiting example, the composition includes a strain of viable Roseomonas mucosa and a strain of viable Pseudomonas aeruginosa. In other specific non-limiting examples, the composition includes 2, 3, 4 or 5 strains of viable Roseomonas mucosa and 2, 3, 4 or 5 strains of viable Pseudomonas aeruginosa.

Thus, pharmaceutical compositions can include two types of gram negative bacteria ("binary combinations" or "binary pairs") or more than two types of gram negative bacteria. In some embodiments, a pharmaceutical composition can include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29 30, 31, 32, 33, 34, 35, 36, 37, 38, 39, or at least 40, at least 50 or greater than 50 types of gram negative bacteria, as defined by genus, species and/or operational taxonomic unit (OTU), such as a strain. Generally the genus, species or strain individually or in combination, have the following characteristics: a) a lysate and/or component of the gram negative bacteria inhibits growth of S. aureus in an in vitro assay; b) the gram negative bacteria stimulates human keratinocytes; c) the gram negative bacteria induces cytokine expression from human cells; and d) the gram negative bacteria is non-pathogenic when administered to the skin of the subject.

In certain embodiments, the gram negative bacteria is transformed with a heterologous nucleic acid, such as in the form of a plasmid. The expression vector can encode any protein of interest. Exogenous DNA can be introduced into bacterial cells with standard techniques such as electroporation or calcium phosphate-mediated transfection.

In some embodiments, the heterologous nucleic acid is included in a plasmid. A plasmid generally contains multiple genetic elements positionally and sequentially oriented with other necessary genetic elements such that the nucleic acid in a nucleic acid cassette can be transcribed and when necessary translated in the transfected cells. Plasmids include nucleic acids that are DNA derived from a plasmid vector, cosmids, or phagemids wherein one or more heterologous nucleic acid may be inserted. The heterologous nucleic acid can encode a protein of interest, which can be operably linked to a promoter for expression of the gram negative bacteria.

Plasmids generally contain one or more unique restriction sites. In addition, a plasmid can confer some well-defined phenotype on the host organism which is either selectable or readily detected, such as drug resistance. Thus, the plasmid can include an expression cassette, wherein a polypeptide is encoded. Expression includes the efficient transcription of an inserted gene, nucleic acid sequence, or nucleic acid cassette with the plasmid.

In one embodiment, when a circular plasmid is transferred into a bacterial cell, it can be an autonomously replicating, extra-chromosomal DNA molecule, distinct from the normal bacterial genome and nonessential for bacterial cell survival under nonselective conditions. The term "persistent expression" as used herein refers to introduction of genes into the cell together with genetic elements which enable episomal (extra-chromosomal) replication and/or maintenance of the genetic material in the cell. This can lead to apparently stable transformation of the cell without the integration of the novel genetic material into the chromosome of the host cell.

A plasmid can also introduce genetic material into chromosomes of the targeted cell where it integrates and becomes a permanent component of the genetic material in that cell. Gene expression after stable introduction can permanently alter the characteristics of the cell and its progeny arising by replication leading to stable transformation.

Methods for Preparing a Bacterial Composition for Administration

Methods for producing bacterial compositions may include three main processing steps, combined with one or more mixing steps. The steps are: organism banking, organism production, and preservation.

For banking, the strains included in a bacterial composition may be (1) isolated directly from a specimen, such as, but not limited to, human skin, or taken from a banked stock, (2) optionally cultured on a nutrient agar or broth that supports growth to generate viable biomass, and (3) the biomass optionally preserved in multiple aliquots in long-term storage.

The gram negative bacteria can be isolated from the skin of a human subject Generally, the human subject does not have atopic dermatitis, or any other skin condition. Thus, the subject can be healthy, meaning that they do not have any other pathological condition. The subject can be immunocompetent. However, gram negative bacteria can be isolated from other sources, such as commercial sources or environmental samples, and used in the methods and compositions disclosed herein. As disclosed herein any gram negative bacteria is of use, provided a) a lysate and/or component of the gram negative bacteria inhibits growth of S. aureus in an in vitro assay; b) the gram negative bacteria stimulates human keratinocytes; c) the gram negative bacteria induces cytokine expression from human cells; and d) the gram negative bacteria is non-pathogenic when administered to the skin of the subject. The gram negative bacteria can then be propagated.

In embodiments using a culturing step, the agar or broth may contain nutrients that provide essential elements and specific factors that enable growth. A non-limiting example is a medium composed of 0.5 g/L dextrose, 0.5 g/L yeast extract, 0.5 g/L proteose peptone, 0.5 g/L casamino acid, 0.3 g/L dipotassium phosphate, 50 mg/L magnesium sulfate, 0.3 g/L sodium pyruvate. A variety of microbiological media and variations are well known in the art (e.g. R. M. Atlas, Handbook of Microbiological Media (2010) CRC Press). Medium can be added to the culture at the start, may be added during the culture, or may be intermittently/continuously flowed through the culture. The species/strains can be cultivated alone, or as an entire collection comprising the bacterial species/strains. As an example, a first strain may be cultivated together with a second strain in a mixed continuous culture, at a dilution rate lower than the maximum growth rate of either cell to prevent the culture from washing out of the cultivation.

The culture is incubated under favorable conditions for a time sufficient to build biomass. For bacterial compositions for human use this is often at about 32-37° C., pH, and other parameter with values similar to the normal human niche. The environment can be actively controlled.

When the culture has generated sufficient biomass, it may be preserved for banking. The organisms may be placed into a chemical milieu that protects from freezing (such as by adding cryoprotectants), drying, and/or osmotic shock (such as by adding osmoprotectants), dispensing into multiple (optionally identical) containers to create a uniform bank, and then optionally treating the culture for preservation. Containers are generally impermeable and have closures that assure isolation from the environment. Cryopreservation can be accomplished by freezing a liquid at ultra-low temperatures (e.g., at or below about −70° C.). Dried preservation removes water from the culture by evaporation (in the case of spray drying or cool drying) or by sublimation (e.g., for freeze drying, spray freeze drying). Removal of water improves long-term bacterial composition storage stability at higher temperatures. Strains and/or species can be cultured and preserved individually, or species/strains can be mixed together for banking.

In one non-limiting example, for cryopreservation, a bacterial culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. or −70° C. for long-term viability retention. This procedure achieves acceptable viability upon recovery from frozen storage.

Organism production may be conducted using similar steps to banking, including medium composition and culture conditions. Production can be conducted using large scale operation, especially for clinical development or commercial production. At larger scales, there may be several subcultivations of the bacteria prior to the final cultivation. At the end of cultivation, the culture is harvested for formulation into a dosage form for administration. This can involve concentration, removal of undesirable medium components, and/or introduction into a chemical milieu that preserves the bacterial composition and renders it acceptable for administration via the chosen route. For one non-limiting example, a bacterial composition may be cultivated to a concentration of $10^{10}$ CFU/mL with a preservative medium consisting of 15% sucrose in water.

Topical Formulations and Methods of Treatment

Pharmaceutical compositions are provided that include the disclosed isolated or substantially purified gram negative bacteria, wherein the pharmaceutical composition is formulated for topical administration. These compositions include a pharmaceutically acceptable carrier, and optionally include additional compounds. In some embodiments, the pharmaceutical composition includes additional active and/or inactive materials in order to produce a final product, which may be in single dosage unit or in a multi-dose format.

Any subject that has atopic dermatitis can be treated using the methods disclosed herein. The subject can be a human. In some embodiments, the subject is a child, such as a subject that is 11, 10, 9, 8, 7, 6, 5, 4, 3, 2 or 1 year(s) of age or less. The subject can be an infant, such as a subject of less than 1 year of age. In other embodiments, the subject is an adult, such as subject who is 18 years of age, greater than 20, 25, 30, 35, 40, 45, 50, 55, or 60 years of age. The subject can be a senior, such as a subject who is greater than 65, 70, 75, or 80 years of age. The subject can be immunocompromised or can have an intact immune system (immunocompetent).

In some embodiments the pharmaceutical composition can include one or more of a buffering agent, a preservative, a stabilizer, a binder, a compaction agent, a lubricant, a dispersion enhancer and/or a coloring agent. Non-limiting examples of suitable buffering agents include sodium citrate, magnesium carbonate, magnesium bicarbonate, calcium carbonate, and calcium bicarbonate. Non-limiting examples of suitable preservatives include antioxidants, such as alpha-tocopherol and ascorbate, parabens, chlorobutanol, and phenol. Non-limiting examples of suitable binders include sucrose, starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. A pH buffering agent(s) can, if employed and when dissolved in an aqueous component of the composition, provide a pH in the range of 5 to 7 (e.g. about pH 5.5).

The pharmaceutical composition can include other ingredients, such as to sustain growth of the bacteria. In some embodiments, the pharmaceutical composition can include a nutrient. In some embodiments the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers.

In some embodiments the composition includes at least one lipid. A "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0).

In some embodiments the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In additional embodiments the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

Various other additives may be included in the compositions. These include, but are not limited to, antioxidants, astringents, perfumes, preservatives, emollients, pigments, dyes, humectants, propellants, and sunscreen agents, as well as other classes of materials whose presence may be pharmaceutically or otherwise desirable. Non-limiting examples of optional additives are as follows: preservatives such as sorbate; solvents such as isopropanol and propylene glycol; astringents such as menthol and ethanol; emollients such as polyalkylene methyl glucosides; humectants such as glycerine; emulsifiers such as glycerol stearate, PEG-100 stearate, polyglyceryl-3 hydroxylauryl ether, and polysorbate 60; sorbitol and other polyhydroxyalcohols such as polyethylene glycol; sunscreen agents such as octyl methoxyl cinnamate (available commercially as Parsol MCX) and butyl methoxy benzoylmethane (available under the tradename Parsol 1789); antioxidants such as ascorbic acid (vitamin C), a-tocopherol (Vitamin E), β-tocopherol, γ-tocopherol, δ-tocopherol, ε-tocopherol, ζι-tocopherol, Ẑ-tocopherol, η-tocopherol, and retinol (vitamin A); essential oils, ceramides, essential fatty acids, mineral oils, vegetable oils (e.g., soya bean oil, palm oil, liquid fraction of shea butter, sunflower oil), animal oils (e.g., perhydrosqualene), synthetic oils, silicone oils or waxes (e.g., cyclomethicone and dimethicone), fluorinated oils (generally perfluoropolyethers), fatty alcohols (e.g., cetyl alcohol), and waxes (e.g., beeswax, carnauba wax, and paraffin wax); skin-feel modifiers; and thickeners and structurants such as swelling clays and cross-linked carboxypolyalkylenes.

Other additives include materials that condition the skin (particularly, the upper layers of the skin in the stratum corneum) and keep it soft by retarding the decrease of its water content and/or protect the skin. Such conditioners and moisturizing agents include, by way of example, pyrrolidine carboxylic acid and amino acids; organic antimicrobial agents such as 2,4,4'-trichloro-2-hydroxy diphenyl ether (triclosan) and benzoic acid. Further additives include anti-inflammatory agents such as acetylsalicylic acid and glycyrrhetinic acid; anti-seborrhoeic agents such as retinoic acid; vasodilators such as nicotinic acid; inhibitors of melanogenesis such as kojic acid; and mixtures thereof.

In other embodiments, the composition can include alpha hydroxyacids, alpha ketoacids, polymeric hydroxyacids, moisturizers, collagen, marine extract, and antioxidants such as ascorbic acid (vitamin C) and/or a-tocopherol (Vitamin E). Sunscreens may also be included. Additional, components such as enzymes, herbs, plant extracts, glandular or animal extracts can be added to the composition. The amounts of these various additives are those conventionally used in the cosmetics field, and range, for example, from about 0.01% to about 20% of the total weight of the topical formulation.

The compositions can also include antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof.

The compositions can also contain irritation-mitigating additives to minimize or eliminate the possibility of skin irritation or skin damage resulting from the chemical entity to be administered, or other components of the composition. Suitable irritation-mitigating additives include, for example: a-tocopherol; monoamine oxidase inhibitors, particularly phenyl alcohols such as 2-phenyl-1-ethanol; glycerin; salicylates; ascorbates; ionophores such as monensin; amphiphilic amines; ammonium chloride; N-acetylcysteine; capsaicin; and chloroquine. The irritation-mitigating additive, if present, can be incorporated into the compositions at a concentration effective to mitigate irritation or skin damage, typically representing not more than about 20 wt. %, more typically not more than about 5 wt. %, of the formulation.

Further suitable pharmacologically active agents that may be incorporated into the present formulations in certain embodiments and thus topically applied along with the active agent include, but are not limited to, the following: agents that improve or eradicate pigmented or non-pigmented age spots, keratoses, and wrinkles; local anesthetics and analgesics; corticosteroids; retinoids; and hormones. Some examples of topical pharmacologically active agents include acyclovir, amphotericins, chlorhexidine, clotrimazole, ketoconazole, econazole, miconazole, metronidazole, minocycline, phenytoin, para-amino benzoic acid esters, octyl methoxycinnamate, octyl salicylate, oxybenzone, dioxybenzone, tocopherol, tocopheryl acetate, zinc pyrithione, diphenhydramine, pramoxine, lidocaine, procaine, crotamiton, hydroquinone and its monomethyl and benzyl ethers, naproxen, ibuprofen, cromolyn, retinol, retinyl palmitate, retinyl acetate, coal tar, griseofulvin, estradiol, hydrocortisone, hydrocortisone 21-acetate, hydrocortisone 17-valerate, hydrocortisone 17-butyrate, progesterone, betamethasone valerate, betamethasone dipropionate, triamcinolone acetonide, fluocinonide, clobetasol propionate, minoxidil, dipyridamole, diphenylhydantoin, benzoyl peroxide, 5-fluorouracil, tacrolimus, and topical steroids such as alclometasone, amcinonide, betamethasone, clobetasol, desonide, dexoximetasone, diflorasone, flucinonide, flurandrenolide, halobetasol, halcinonide, hydrocortisone, and/or triamcinolone.

Although topical formulations, such as creams and salves formulated for dermal delivery are contemplated, the delivery systems can include time-release, delayed release or sustained release delivery systems. Such systems can avoid repeated administrations of the compositions, increasing convenience to the subject and the physician. Many types of release delivery systems are available and known to those of ordinary skill in the art. Specific examples include, but are not limited to: (a) erosional systems such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480.

The delivery system can include collagen, fibrin, or a membrane extract, such as a basal membrane extract, for example wherein the composition is formulated for administration to the skin. Suitable basement membrane extracts include a biologically active polymerizable extract containing in parts by weight about 60-85% laminin, 5-30% collagen IV, 1-10% nidogen, 1-10% heparan sulfate proteoglycan and 1-5% entactin (see U.S. Pat. No. 4,829,000, incorporated herein by reference, which discloses BME compositions as well as methods for producing these compositions). BME can support normal growth and differentiation of various cell types including epithelial cells when cultured. Basal membrane extracts are well known in the art and are commercially available.

For treatment of the skin, a therapeutically effective amount of the composition can be locally administered to the affected area. The pharmacological compositions disclosed herein facilitate the use of at least gram negative bacterium for the treatment of atopic dermatitis. Such a composition can be suitable for delivery of the active ingredient to any suitable subject, such as but not limited to, a human subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically, as discussed above.

A composition can contain a single (unit) dose of gram negative bacteria. Exemplary amounts are $10^5$-$10^{12}$ colony forming units (cfu) such as $10^6$-$10^{10}$, for example, $10^5$-$10^7$ cfu, for example $10^6$ cfu. In some embodiments, suitable doses of gram negative bacteria can be in the range $10^4$ to $10^{12}$ cfu, e.g. one of $10^4$ to $10^{10}$, $10^4$ to $10^8$, $10^6$ to $10^{12}$, $10^6$ to $10^{10}$, or $10^6$ to $10^8$ cfu. In other embodiments the composition can include at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, about 50.0% by weight of bacteria. In other embodiments the composition can include at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to 10 about 5%, by weight of the gram negative bacteria.

The composition can be applied to the skin, such as at lesion areas and round lesion area, or at areas of intact skin (non-lesion areas) to prevent lesions for forming. The composition can be used to reduce lesion size. The composition can be applied daily. The composition can be applied 1, 2, 3, 4, or 5 time per day. The composition can be applied every other day, or 1, 2, 3, 4, 5, 6, or 7 times per week. The composition can be applied weekly. In one specific, non-limiting example, $10^6$ cfu is applied to the skin 2 or 3 times per week. The composition can be formulated as a unit dose for administration.

Methods of producing topical pharmaceutical compositions such as creams, ointments, lotions, sprays and sterile aqueous solutions or suspensions are well known in the art. Suitable methods of preparing topical pharmaceutical compositions are described, for example in PCT Publication No. WO 95/10999. PCT Publication No. WO2012150269, U.S. Pat. No. 6,974,585, and PCT Publication No. WO 2006/048747, all incorporated herein by reference. The composition can include an aqueous carrier, and be applied as a spray to the skin.

Optionally, a composition can include a pharmaceutically acceptable viscosity enhancer and/or film former. A viscosity enhancer increases the viscosity of the formulation so as to inhibit its spread beyond the site of application. Balsam Fir (Oregon) is an example of a pharmaceutically acceptable viscosity enhancer of use with gram negative bacteria.

A film former, when it dries, forms a protective film over the site of application. The film inhibits removal of the active ingredient and keeps it in contact with the site being treated. An example of a film former that is suitable for use in this invention is Flexible Collodion, USP. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints. Creams, as is well known in the arts of pharmaceutical formulation, are viscous liquids or semisolid emulsions, either oil-in-water or water-in-oil.

Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Lotions, are preparations to be applied to the skin surface without friction, and are typically liquid or semiliquid preparations in which particles, including the active agent, are present in a water or alcohol base. Lotions are usually suspensions of solids, and preferably, comprise a liquid oily emulsion of the oil-in-water type. Lotions can be used for treating large body areas, because of the ease of applying a more fluid composition. It is generally necessary that the insoluble matter in a lotion be finely divided.

Lotions typically contain suspending agents to produce better dispersions as well as compounds useful for localizing and holding the active agent in contact with the skin, e.g., methylcellulose, sodium carboxymethyl-cellulose, or the like.

Solutions are homogeneous mixtures prepared by dissolving one or more chemical substances (solutes) in a liquid such that the molecules of the dissolved substance are dispersed among those of the solvent. The solution may contain other pharmaceutically or cosmetically acceptable chemicals to buffer, stabilize or preserve the solute. Common examples of solvents used in preparing topical solutions are ethanol, water, propylene glycol or any other acceptable vehicles. These can be applied in any manner, such as spraying them on the skin, painting them on the skin, or wetting a bandage with the solution.

Gels are semisolid, suspension-type systems. Single-phase gels contain organic macromolecules distributed substantially uniformly throughout the carrier liquid, which is typically aqueous, but also, preferably, contain an alcohol, and, optionally, an oil. Some "organic macromolecules," of use, specifically gelling agents, are crosslinked acrylic acid polymers such as the "carbomer" family of polymers, e.g., carboxypolyalkylenes that re commercially available as CARBOPOL®. Also of use are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. These gels are of use in the methods disclosed herein.

Ointments can also be used in the disclosed methods. Ointments are semisolid preparations that are typically based on petrolatum or other petroleum derivatives. The specific ointment base to be used, as will be appreciated by those skilled in the art, is one that will provide for a number of desirable characteristics, e.g., emolliency or the like. An ointment base is generally inert, stable, nonirritating, and nonsensitizing. Ointment bases are grouped in four classes: oleaginous bases; emulsifiable bases; emulsion bases; and water-soluble bases (see Remington: The Science and Practice of Pharmacy, 19th Ed. (Easton, Pa.: Mack Publishing Co., 1995), at pages 1399-1404). Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin, and hydrophilic petrolatum. Emulsion ointment bases are either water-in-oil (W/O) emulsions or oil-in-water (O/W) emulsions, and include, for example, acetyl alcohol, glyceryl monostearate, lanolin, and stearic acid. Water-soluble ointment bases are prepared from polyethylene glycols of varying molecular weight.

Pastes are semisolid dosage forms in which the active agent is suspended in a suitable base, and are also of use. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

A topical composition can any form suitable for application to the body surface, such as a cream, lotion, sprays, solution, gel, ointment, paste, plaster, paint, bioadhesive, bandage, sprays, suspensions or the like, and/or may be prepared so as to contain liposomes, micelles, and/or microspheres. A topical composition can be used in combination with an occlusive overlayer so that moisture evaporating from the body surface is maintained within the formulation upon application to the body surface and thereafter.

A cream, lotion, gel, ointment, paste or the like may be spread on the affected surface. A solution may be applied in the same way, but more typically will be applied with a dropper, swab, sprayer or the like, and carefully applied to the affected areas. The composition can be applied directly to the target location, for example in a topical preparation such as an ointment, or as a part of a dressing or a bandage. The composition can be formulated as a unit dosage, for administration by any device for administration to the skin. The unit dosage may be a reservoir of the active agent in a carrier, for example an adhesive carrier capable of adhering to the skin for a desired period of time such as at least a day or more.

The pharmaceutical compositions are of use for the treatment of atopic dermatitis. Thus, in some embodiments, topical application results in reduced lesion size, reduce number of lesions, and/or a reduction in symptoms. The application of these pharmaceutical compositions can reduce S. aureus in the skin of the subject being treated. The application of the pharmaceutical composition can provide enhanced barrier function of the skin as measured by transepidermal water loss.

Atopic dermatitis occurs as flare-ups, and there can be periods of remission. The topical application can reduce reoccurrences, so that additional incidents of atopic dermatitis are reduced in number, intensity, or frequency. The topical application can increase the time of remission, such as the length of time between incidents. In some embodiments, an additional incident of atopic dermatitis will not occur for 1, 2, 3, 4, 5, 6, 7, 8, 9, 10, 11, or 12 weeks following application. In an additional embodiment, an additional incident of atopic dermatitis will not occur for 1, 2, 3, 4, 5, 6, 7, 8, 9, 10, 11, or 12 months following the topical application.

The method can include measuring the microbiota of the skin of the subject. Specifically, diagnostic assays can be performed to determine if the bacterial taxa in the skin of a subject is altered following treatment. Thus, in some embodiments, it is determined if the bacterial phyla, bacterial classes, bacterial orders, bacterial families, bacterial genera and/or bacterial species are altered in the skin of a subject with atopic dermatitis. In one embodiment, it is determined if the amount of S. aureus is modified in the skin of the subject following treatment.

Such a method for identifying a microbiota in a sample can include providing a sample, such as a skin sample, and detecting at least one microbiota in the sample. One embodiment of the method can include preparing a nucleic acid sample including a molecular indicator of identity from at least one microbiota present in the sample and detecting the molecular indicator of identity. For example, the method can involve preparing at least one nucleic acid sample by preparing a DNA sample. The molecular indicator of identity can be a polymorphic polynucleotide, such as an rRNA gene (for example, a 16S rRNA gene). The molecular indicator of identity can be detected by determining the nucleotide sequence of the polymorphic polynucleotide, such as the 16S rRNA gene, or a portion or subsequence thereof. Additional embodiments for detecting the molecular indicator of identity can also include PCR with selective primers, quantitative PCR with selective primers, DNA-DNA hybridization, RNA-DNA hybridization, in situ hybridization, and combinations thereof. For example, the polymorphic polynucleotide can be detected by hybridization to a specific probe. In such an example, the specific probe hybridizes to a polymorphic target nucleic acid, such as a 16S rRNA gene. Optionally, the nucleic acid can be hybridized to at least one array comprising a plurality of specific probes, e.g., a plurality of specific probes, each of which identifies a bacteria. Detecting the molecular indicator of identity can also be accomplished using protein probes (such as antibodies) that bind to polymorphic target proteins, for example polymorphic target proteins that identify the microbiota (see U.S. Pat. No. 9,173,910, incorporated herein by reference).

The relative abundance of one or more bacteria, such as S. aureus, can be measured in a sample from a subject. As used herein, the term "relative abundance" refers to the commonality or rarity of an organism relative to other organisms in a defined location or community. For example, the relative abundance can be determined by generally measuring the presence of a particular organism compared to the total presence of organisms in a sample.

The relative abundance of bacteria can be measured directly or indirectly. Direct measurements can include culture based methods. Indirect measurements can include comparing the prevalence of a molecular indicator of identity, such as ribosomal RNA (rRNA) gene sequences, specific for an organism or group of organisms in relation to the overall sample.

In one embodiment, the relative abundance of microbiota, such S. aureus and/or any type of gram negative bacteria, within the skin an individual subject may be calculated by measuring the ratio of one or more specific bacteria in a sample from an individual to obtain a microbiota profile of the subject. The relative abundance can be derived from the total abundance of bacteria present in a sample. As used herein, the "total abundance" refers generally to the total bacteria in a sample. Thus, a "microbiota profile" refers to a representation, such as a graph, of the relative abundance of one or more microbiota in a subject or sample of skin from a subject.

Kits

The disclosed a therapeutically effective amount of a purified viable gram negative bacteria can be provided as components of a kit. The purified viable gram negative bacteria can be provided in a growth medium, in a lyophilized form, or as frozen cells. Thus, the kit can include a container comprising a therapeutically effective amount of a purified viable gram negative bacteria, wherein i) a lysate and/or component of the gram negative bacteria inhibits growth of S. aureus in an in vitro assay; ii) the gram negative bacteria stimulates human keratinocytes iii) the gram negative bacteria induces cytokine expression from human cells; and iv) the gram negative bacteria is non-pathogenic when administered to the skin of the subject.

In some embodiments, the kit can include the components needed to produce a pharmaceutical composition, such as one container including the gram negative bacteria (in any form) and one container including a pharmaceutically acceptable carrier for suspending the gram negative bacteria thereof. The pharmaceutically acceptable carrier can be, for example, a buffered saline solution or a sucrose solution. In other embodiments, the kit can include a container including the gram negative bacteria, and a second container including a pharmaceutically acceptable carrier, and a device, such as, but not limited to, a syringe, for measuring the pharmaceutically acceptable carrier. In yet another embodiment, the kit can include a device, such as, but not limited to, a spray nozzle or a bandage, for topical application of the gram negative bacteria once it is suspended in the pharmaceutically acceptable carrier.

Optionally, such a kit includes additional components including packaging, instructions and various other reagents, such as additional buffers or other therapeutic ingredients. The kit can include a container and a label or package insert on or associated with the container. Suitable containers include, for example, bottles, vials, tubes, etc. The containers may be formed from a variety of materials such as glass or plastic. The container typically holds a composition including the gram negative bacteria which is effective for treating atopic dermatitis. In several embodiments the container may have a sterile access port (for example the container may be an intravenous solution bag or a vial having a stopper pierceable by a hypodermic injection needle). The label or package insert indicates that the composition is used for treating the particular condition, such as atopic dermatitis.

The label or package insert typically will further include instructions for use. The package insert typically includes instructions customarily included in commercial packages of therapeutic products that contain information about the indications, usage, dosage, administration, contraindications and/or warnings concerning the use of such therapeutic products. In some non-limiting examples, the instructions include information on the amount of the pharmaceutically acceptable carrier to add to the vial containing the gram negative bacteria, instructions for suspending the gram negative bacteria in the pharmaceutically acceptable carrier, and instructions for topical application to the skin. The application can be spraying on the skin, swabbing on the skin, or introducing the suspension onto a bandage for application to the skin.

The instructional materials may be written, in an electronic form (such as a computer diskette or compact disk) or may be visual (such as video files). The kits may also include additional components to facilitate the particular application for which the kit is designed, such as spray tips, bandages, or swabs for dermal application. The kits may additionally include buffers and other reagents routinely used for the practice of a particular method. Kits and appropriate contents are well known to those of skill in the art.

The disclosure is illustrated by the following non-limiting Examples.

EXAMPLES

Studies were performed to evaluate if immunologic outcomes differ after exposure to different commensal gram negative (CGN) bacteria collected from human skin. For these studies, CGN bacteria were collected from healthy controls and patients with atopic dermatitis (AD). Using various cellular and culture-based models, their immunogenicity was evaluated. Representative strains of CGN were selected, and their impact was evaluated in the MC903 mouse model of AD. It was found that CON bacteria taken from healthy human volunteers but not from patients with AD were associated with enhanced barrier function, innate immunity activation, and control of *S. aureus*. Treatment of AD with CON from healthy controls improved outcomes in a mouse model.

Example 1

Materials and Methods

Gram Negative Bacterial Collection and Identification:

Two FloqSwabs (Copan, Brescia, Italy) moistened in sterile phosphate buffered saline (PBS; Corning Cellgro, Corning, N.Y.) were rubbed on the subject's skin (at the antecubital fossa) vigorously for 15-30 seconds. One swab was placed into a 15 mL conical tube (Corning Life, Corning, N.Y.) with 2 mL of sterile Hank's balanced salt solution (HBSS; Sigma-Aldrich) containing vancomycin (300 ug/mL) and amphotericin B (5 ug/mL; Sigma-Aldrich, St. Louis, Mo.) to inhibit growth of gram positive bacteria and fungi. The remaining swab was placed into a 15 mL conical tube containing 2 mL of R2A (Reasoner's 2A) broth (Teknova, Hollister, Calif.) with similar concentrations of vancomycin and amphotericin B. The tubes, with swabs left in place, were then incubated at 32° C. with constant shaking for 48-72 hours before plating 100 uL from each tube onto an R2A agar plate (Remel, Lenexa, Kans.). Colonies were then taken for species identification by mass spectrometry using matrix-assisted laser desorption/ionization-time of flight (MALDI-TOF) analysis. Bacterial protein extraction for MALDI-TOF MS using the BioTyper (v3.1, Bruker Daltonics Inc., Billerica, Mass.) was performed by the NIH Clinical Center microbiology lab using previously described methods (Lau et al., *Journal of clinical microbiology* 52, 2804-2812 (2014); published online Epub August (10.1128/JCM.00694-14), instrument settings and calibration (Lau et al., *Journal of clinical microbiology* 51, 828-834 (2013); published online (Epub) March (10.1128/JCM.02852-12); Youn et al., *Journal of clinical microbiology*. (2015); published online (Epub) September 2 (10.1128/JCM.01643-15)). BioTyper identification was supplemented by additional mass spectra profiles provided by several NIH developed databases (Lau et al, 2014, supra; Stevenson et al., *Journal of clinical microbiology* 48, 3482-3486 (2010); published online (Epub) October (10.1128/JCM.00687-09; Myles et al., *Nature immunology* 14, 804-811 (2013); published online (Epub) August (10.1038/ni.2637)). Ten of the healthy control *R. mucosa* strains reported in FIG. 1 were identified based solely on the unique colony morphology, UV light reactivity, and Gram-stain characteristics that had been observed in the other *R. mucosa* isolates identified by MALDI-TOF analysis. All *R. mucosa* isolates used for subsequent studies were verified by MALDI-TOF analysis. Written informed consent was obtained for all participants in this study.

In Vitro *Staphylococcus aureus* Inhibition Assay:

Gram negative isolates were cultured as above in 5 mL of R2A for 8-10 days. Bacteria were pelleted at 5000 g for 12 minutes. Supernatants were harvested, frozen, then lyophilized (Labconco FreeZone 2.5, Kansas City, Mo.). The lyophilized product, and a control of concurrently incubated and lyophilized R2A without bacteria, were suspended in 1 mL of tryptic soy broth (TSB). An overnight culture of *S. aureus* strains grown in 5 mL TSB was diluted 1:100 into fresh media then 100 mcL of the newly diluted culture was combined with 100 mcL of the TSB containing the CGN supernatant or lyophilized R2A control. Samples were incubated for 3 hours at 37° C. under constant agitation. Serial dilutions were performed and plated; the following day colonies were counted and averaged across all countable plates. Percent impact on *S. aureus* growth was calculated by dividing the number of CFU in the CGN-supernatant exposed culture by the number of CFU in the R2A-only exposed culture.

Blister Induction and Bacterial Challenge:

An eight-well suction chamber was designed (Ammnra Creations; San Jose, Calif.) and 3D printed in bronze (Shapeways; New York, N.Y.). This was placed onto the participants' ethanol-sterilized volar forearm, and placed under 30 mm Hg of suction for 2 hours using a microderm abrasion device (Kendal Diamond HB-SF02). After device removal, the resultant epidermal blister roofs were surgically removed. Eight challenge chambers were designed (Ammnra Creations) and 3D printed in bronze (Shapeways) (FIG. 4C). Using a matching eight well template (Ammnra Creations), 10 mm punch biopsies (Acu-Punch, Acu-derm; Fort Lauderdale, Fla.) were cut into one 4"×4" Duoderm dressing (ConvaTec; Bridgewater, N.J.). The rims of the challenge chambers were brushed with Dermabond adhesive (Ethicon; Somerville, N.J.) before being placed over the denuded blisters. Each well was filled with 1 mL of either sterile saline (Corning Life) or 2e7 CFU of irradiated bacteria suspended in sterile saline. Blister fluid was removed via pipette (Eppendorf; Hauppauge, N.Y.) the following morning. Collected samples were centrifuged at 350 g for 7 minutes, supernatants were removed and frozen for batch analysis.

Cytokine and Anti-Microbial Peptide Detection:

Standards of human reg3gamma (Sino Biologicals; Beijing, China) or blister fluid samples (100-12.5% diluted in 0.9% NaCl) were coated on Nunc Maxisorp plates overnight. The next day, wells were washed 5× with PBS and blocked in 3% BSA in PBS for 1 h. Wells were washed once with PBS. Polyclonal, protein A-purified rabbit anti-mouse reg3gamma (13.2 mg/ml; kind gift from J. Kolls. University of Pittsburgh) was added at a 1:1000 dilution in 1% BSA/PBS and incubated 90 min at RT. Anti-rabbit HRP (Santa Cruz; Dallas, Tex.) and TMB substrate (Ebioscience; San Diego, Calif.) were added and plate was incubated at RT for 5-10 min. 2N $H_2SO_4$ was added to stop the reaction; plates were read at 450 nm. LL-37 (Hycult; Plymouth Meeting, Pa.) and human beta-defensin 3 (PeproTech; Rocky Hill, N.J.) were measured by commercial ELISA kits. Cytokine levels were determined by Bio-Plex (BIO-Rad; Hercules, Calif.) per manufacturer instructions.

Keratinocyte Cultures:

Primary foreskin keratinocyte (KC) cultures were collected and stimulated as previously described (Myles et al., *Nature immunology* 14, 804-811 (2013); published online EpubAug (10.1038/ni.2637)). 1e7 CFU of live commensal gram negative bacteria were added to KC culture media. mRNA was extracted after 24 hours for PCR analysis by the Δ Δ CT method.

Mice:

BALB/c mice were purchased from Taconic Farms (Hudson, N.Y.). Mice were used between 8 and 14 weeks of age. Experiments were performed in both male and female mice, but age and sex matched within each experiment.

Trans-Epidermal Water Loss (TEWL) Measurements:

Mice were shaved and hair chemically removed (Nair). Starting the following day, approximately 1e7 CFU of live bacteria were placed on the nude areas daily. Immediately prior to inoculation. TEWL was measured daily by VapoMeter (Delfin; Greenwich, Conn.), per manufacturers instructions.

MC903 and Ear Inoculations:

MC903 mouse model of AD was performed as previously described (Wang et al., *The Journal of allergy and clinical immunology* 135, 781-791 e783 (2015); published online (Epub) March (10.1016/j.jaci.2014.09.015)). For prevention studies, 1e7 CFU of gram negative bacteria were suspended in sterile PBS and dripped onto the mouse ears in 10 mcL of volume. Inoculations were initiated two days prior to MC903, and continued throughout the MC903 exposure. MC903 was placed first, the ethanol was allowed to evaporate for 2-5 minutes prior to placement of bacterial isolates. Ear thickness was measured on day 14. mRNA isolation and PCR were performed as previously described (Myles et al., 2013, supra). For experiments using co-inoculation of *S. aureus*, 1e6 CFU of the SAAS9 strain of *S. aureus* was dripped onto the ear immediately prior to inoculation with the gram negative isolate. Treatment studies were performed by exposing mice to MC903 daily for 14 days and inoculating with 1e7 CFU of gram negative bacteria on days 13-15. Ear thickness was measured and photos taken on day 21.

Serum Total IgE Analysis:

Serum was collected on day 14 of MC903 treatment. Total IgE was determined as previously described (Myles, *Nutrition journal* 13, 61 (2014)10.1186/1475-2891-13-61)) using a commercial kit (Bethyl Laboratories, Montgomery, Tex.).

Statistics:

Means were compared using two-tailed unpaired t Lest, or ANOVA for comparison of multiple samples, with Prism software (GraphPad, San Diego, Calif.). NS=not significant, *=p<0.05, =p<0.01, *=p<0.001. ****=p<0.0001.

Study Approval:

All animal experiments were conducted under approved Office of Animal Care and Use procedures. All human sample collection and processing was performed under IRB approved clinical trials and all subjects gave full consent to sample collection. All participants provided their written consent to the research protocol and institutional review board (IRB) consent was obtained prior to blood collection.

Example 2

Skin Commensal Gram Negative Microbiota Differ Between Healthy Controls and Patients with AD Genetic-based microbiome identification has revealed significant differences in the gram negative skin biome between AD patients and healthy controls (4). A method for culturing gram negative skin flora through appropriate selection of media, antibiotics and temperature allowed for functional characterization and comparison of CON species. Significant differences were found in the culturable bacteria present on the skin of 17 AD patients as compared to 26 healthy volunteers FIG. 1A; Table 1).

TABLE 1

Demographics of controls and patients.

| Demographic | Controls | Patients | Significance |
|---|---|---|---|
| Number | 26 | 17 | — |
| Age | | | |
| Mean (range) | 32.5 (8-65) | 18.5 (8-51) | ** |
| Sex (%) | | | |
| Male | 50 | 70 | NS |
| Female | 50 | 30 | |
| Race (%) | | | |
| White | 39 | 47 | NS |
| Black | 15 | 18 | |
| Latino | 0 | 0 | |
| Asian | 31 | 24 | |
| Other/Mixed | 15 | 11 | |
| SCORAD (range) | 0 (0) | 19.7 (1-56) | **** |

Age, sex, race, and SCORAD for participants included in FIG. 1. Significance determined by Student's t test (age, SCORAD) or Chi squared (sex, race).
** = p < 0.01,
**** = p < 0.001,
NS = not significant.

The predominant gram negative species identified in healthy volunteers (HV) was *Roseomonas mucosa*. Roughly half of AD patients did not have any culturable gram negative bacteria, consistent with DNA-based analysis (Kong et al., *Genome research* 22, 850-859 (2012); published online EpubMay (10.1101/gr.131029.111)).

Example 3

CGN from Healthy Volunteers Inhibit the Growth of *S. aureus*

Figure 1B:
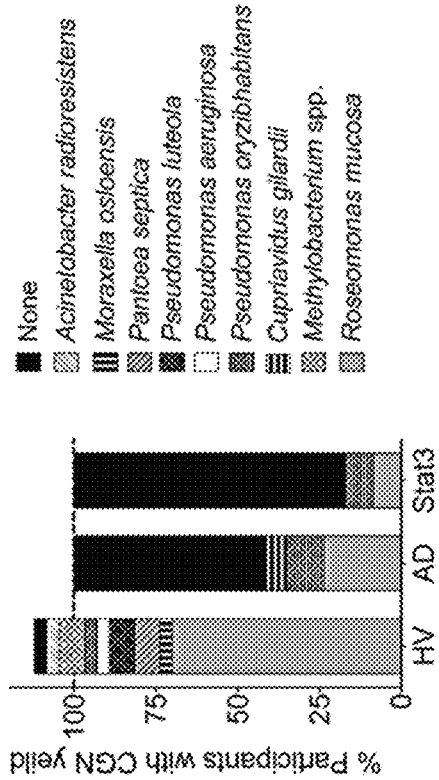
Figure 1C:
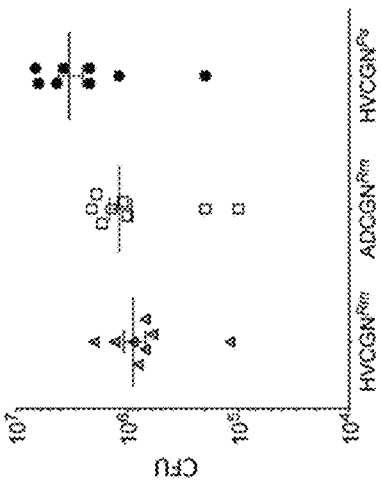
Figure 1D:
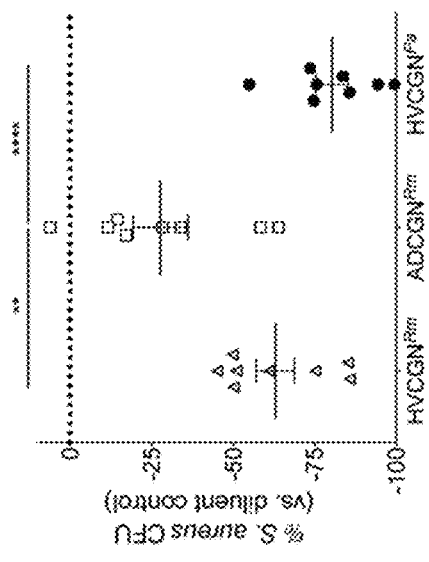
Figure 4:
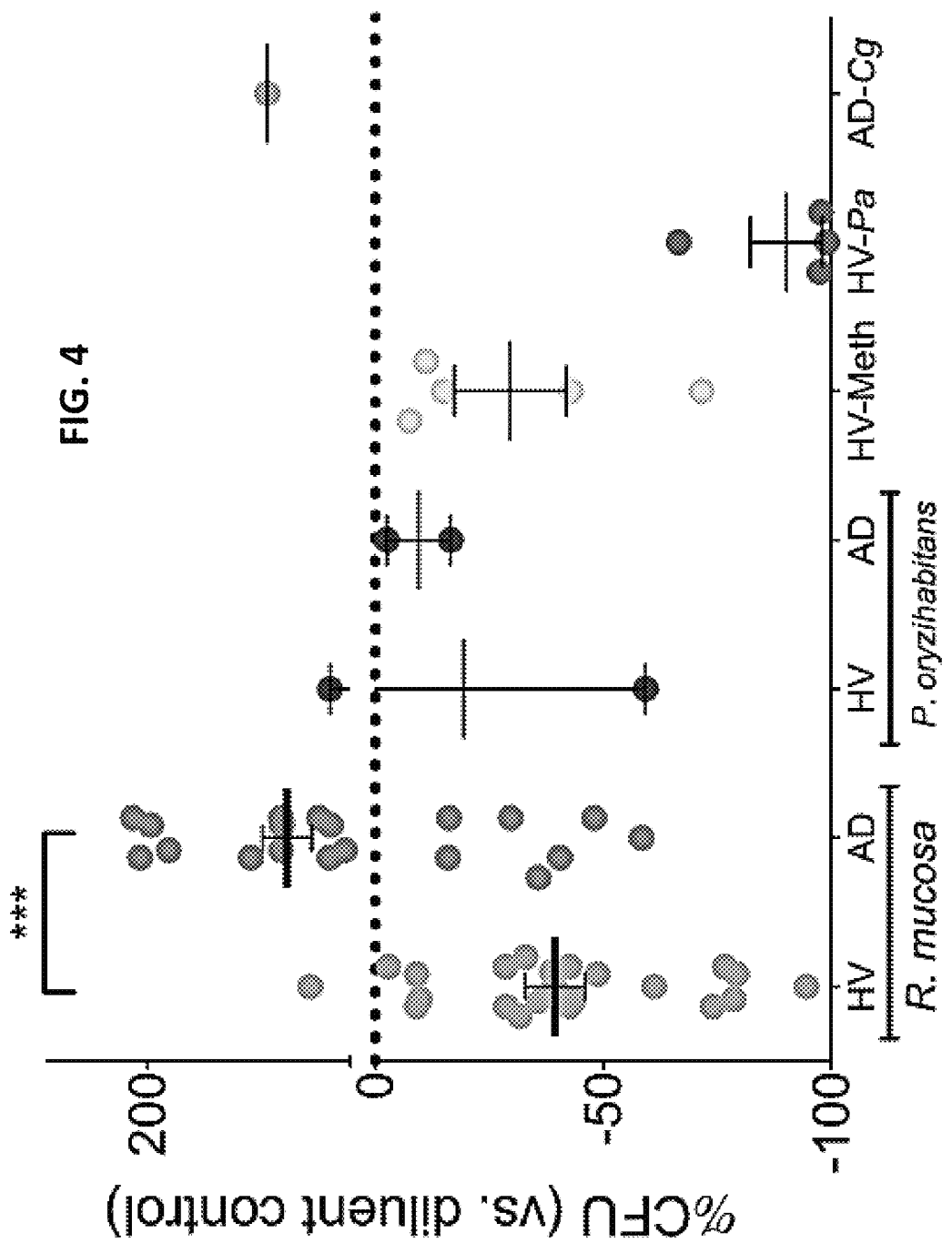
FIG. 4: Species analysis of data from FIG. 1B. Eight strains of *S. aureus* isolated from HV and AD patients were grown in the presence of either CGN supernatant or control media. Each data point represents the effect on *S. aureus* growth of supernatant from one CGN isolate compared to media control (HV isolates=9. AD isolates=7). Significance between *R. mucosa* isolates determined by Student t-test.
Figure 8A:
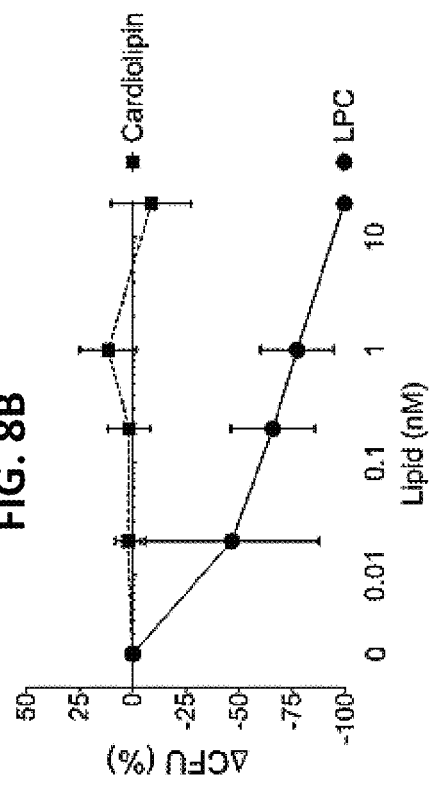
FIGS. 8A-8C. Lipids produced by HV-*R. mucosa* Inhibit *S. aureus* growth. (A) Ammonium sulfate precipitation was performed on supernatants from *R. mucosa* and *P. aeruginosa* prior to evaluating the *S. aureus* (strain USA300) inhibition as performed in FIG. 1B. (B) Three isolates of *S. aureus* were cultured in the presence or absence of lysophosphatidylcholine (LPC) or cardiolipin with inhibition assessed as in FIG. 1B versus diluent (0). (C) Human foreskin keratinocytes were cultured in the presence or absence of LPC were assessed. Data is representative of three independent experiments and displayed as mean±sem. Significance determined by ANOVA with Bonferroni's correction. $*=p<0.05$.
Figure 8C:
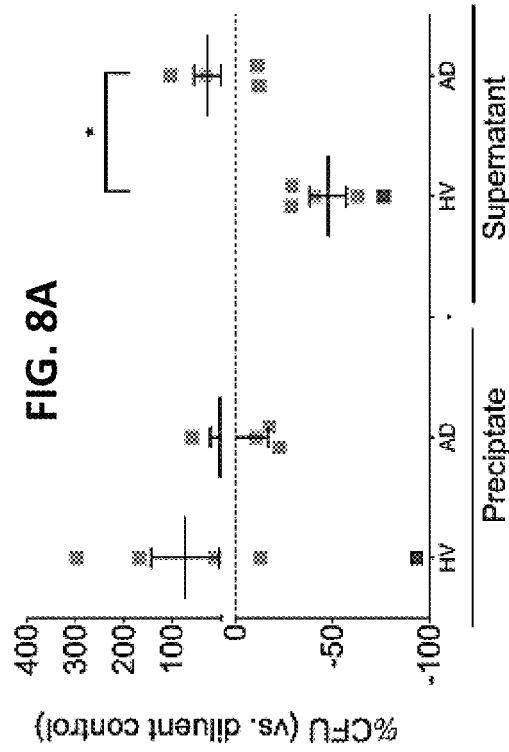
Figure 8B:
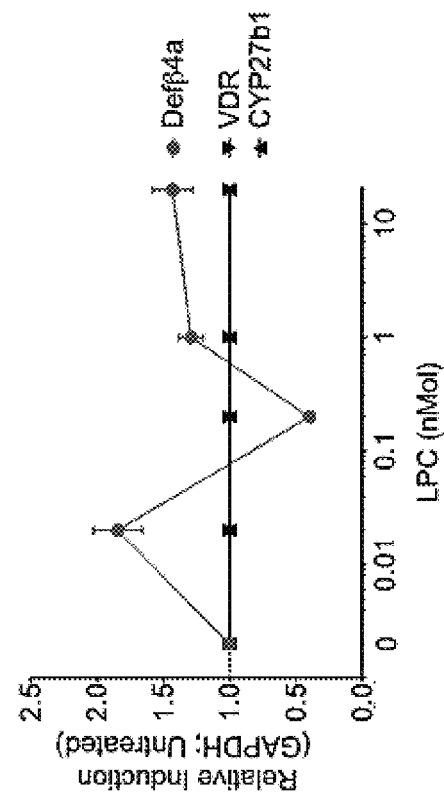

Overgrowth and infection with *S. aureus* is both a contributor to, and consequence of the immune imbalance and poor barrier function characteristic of AD. *S. aureus* can directly activate allergic mast cells (Schlievert et al., *J Allergy Clin Immunol* 125, 39-49 (2010); published online (EpubJan) (10.1016/j.jaci.2009.10.039; Nakamura et al., *Nature* 503, 397-401 (2013); published online (Epub) November 21 (10.1038/nature 12655)) and T-cells (Brauweiler et al., *The Journal of investigative dermatology* 134, 2114-2121 (2014); published online (Epub) August (10.1038/jid.2014.43)). Treatment with antibiotics can reduce *S. aureus* burdens and improve symptoms, but do not normalize the underlying pathology (Boguniewicz and Leung, *J Allergy Clin Immunol* 132, 511-512 e515 (2013); published online (Epub) August (10.1016/j.jaci.2013.06.030)). To evaluate the impact of the CGN strains on *S. aureus* growth, multiple isolates of *S. aureus* were grown in the presence of the supernatant from cultures of CGN. On average, supernatants from HV-CGN inhibited *S. aureus* by nearly 50% (FIG. 1B; FIG. 4). In contrast, AD-CGN had more variable effects, with most strains failing to inhibit (FIG. 1B; FIG. 4). Re-inoculation of *S. aureus* from the inhibitory CON supernatants into fresh media allowed normal growth, suggesting bacteriostatic rather than bactericidal activity. Consistent with this in vitro analysis, co-inoculation of CGN and *S. aureus* on mouse ears also reduced *S. aureus* yields (FIG. 1C). This inhibition was associated with production of the lipid lysophosphatidylcholine (LPC) and recapitulated using commercially purchased LPC (FIG. 8B) indicating unique features of our bacteria were associated with potential clinical benefit.

Example 4

CGN from Healthy Volunteers Induce Innate Immunity in Humans

To measure in vivo human cutaneous immune reactivity to these bacteria, suction blisters were induced on the forearms of healthy volunteers (FIG. 5A) and the epidermal blister roof was removed (FIG. 5B) similarly to what has been previously described (Follin and Dahlgren, *Methods in molecular biology* 412, 333-346 (2007)10.1007/978-1-59745-467-4_22). Challenge chambers (FIG. 5C) were used to expose the dermal blister base to lethally irradiated isolates of either an HV-derived or AD-derived *R. mucosa*, chosen based on their disparate inhibition of *S. aureus* (FIG. 1B).

Figure 2A:
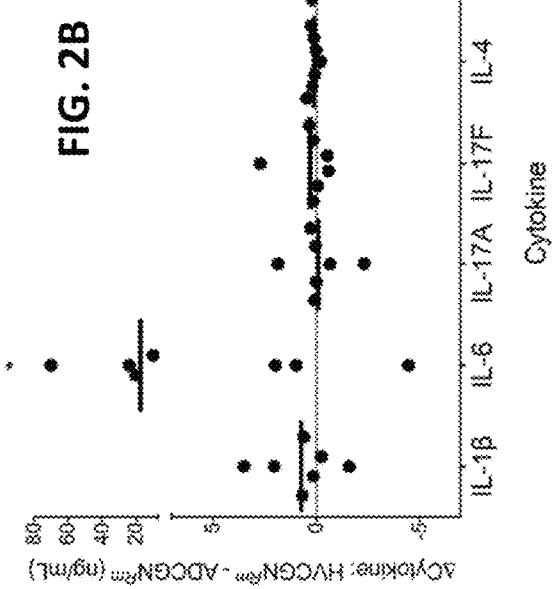
FIGS. 2A-2D: CGN from HV enhances innate immunity and barrier function. (A) Cytokine analysis for in vivo human blister challenge on healthy controls showing cytokine responses to a representative strain of *R. mucosa* from a healthy control versus one isolated from a patient with AD as compared to the saline control well (dotted line), N=7. (B) Paired analysis of data presented in panel A showing the cytokine production in the blister well exposed to the HV sourced *R. mucosa* less the cytokine production in the blister well exposed to the AD sourced *R. mucosa* in the same human subject. (C) Mouse ears were inoculated daily for three days with 1e7 CFU *R. mucosa* from either HV or AD. Day 5 mRNA abundance for IL-1β and filaggrin standardized to GAPDH and compared to untreated mice is shown, N=4-5 mice per group. (D) Mouse backs were shaved and hair chemically removed on day 0. TEWL was then measured after daily application of 1e7 CFU *R. mucosa* from either HV or AD, N=4-5 mice per group. Data shown are a combination of 7 independent experiments (A-B) or representative of two or more independent experiments (C-D) and displayed as mean+sem (C-D) or mean and individual participants (A-B). HV=Healthy Volunteer. AD=Atopic Dermatitis. CGN=Culturable gram negative, Rm=*Roseomonas mucosa*, FLG=filaggrin. IL-=Interleukin, TEWL=Transepidermal Water Loss. Significance from diluent control (or as indicated) determined by ANOVA with Bonferroni's correction.
Figure 2C:
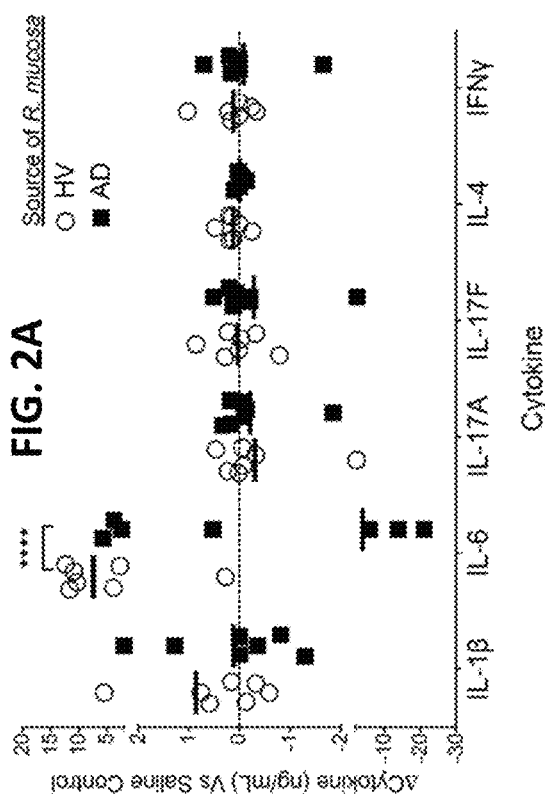
Figure 2B:
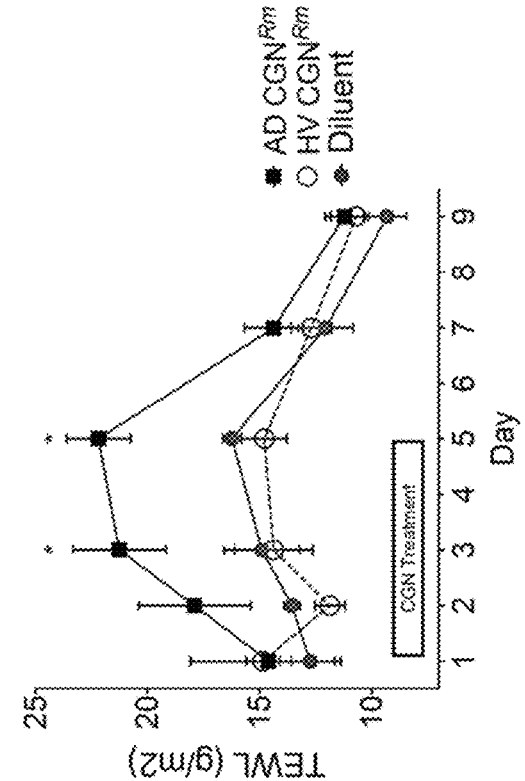

After 20-24 hours of stimulation, blister cytokines levels for IL-6 (FIG. 2A-2B) were significantly higher in response to the HV *R. mucosa* compared to the one from a patient with AD (FIG. 2A-2B). There were no differences in levels of traditional Th (T-helper) cytokines such as interleukin (IL)-17, interferon gamma (IFNγ), or IL-4 (FIG. 2A), nor were there significant differences in levels of many other cytokines (FIG. 6A) or antimicrobial peptides (FIG. 6B); however, adaptive T-cell cytokines should also be measured at later time points. Infection of human foreskin-derived primary keratinocytes (KC) with multiple isolates of live CGN in vitro showed variable effects of the different isolates on KC innate immunity markers, but compared to AD-CGN, HV-CGN enhanced mRNA abundance of defensin MA (FIG. 7A), and the upstream modulators (Miller et al., *Dermatologic therapy* 23, 13-22 (2010); published online (Epub) January-February (10.1111/j.1529-8019.2009.01287.x); Schauber and Gallo, *Experimental dermatology* 17, 633-639 (2008); published online (Epub) August (10.1111/j.1600-0625.2008.00768.x).) CYP27b1 (a vitamin D converting enzyme; FIG. 7B) the vitamin D receptor (VDR) (FIG. 7C), and the anti-microbial peptide cathelicidin (FIG. 7D). There were no differences in transcript levels for IL-1β or IL-6 (FIG. 7E-7F). CD14, IL-8, Tumor Necrosis Factor alpha (TNFα, Toll Like Receptor (TLR) 2, TLR3, TLR4, TLR9, or Thymic stromal lymphopoietin (TSLP) mRNA abundance was also not different, and there was no apparent correlation between the ability of an isolate to inhibit *S. aureus* and activate KC.

Example 5

CGN from Healthy Volunteers Preserves Barrier Function in Mice

Figure 2D:
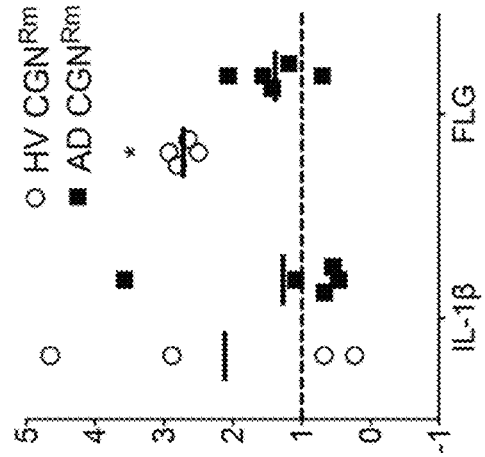

The loss of barrier function in AD causes dry, itchy skin due to trans-epidermal water loss (TEWL) (Boguniewicz et al., *J Allergy Clin Immunol* 125, 4-13; quiz 14-15 (2010); published online (Epub) January (10.1016/j.jaci.2009.11.027)) and cutaneous sensitization to antigens (Pyun, *Allergy, asthma & immunology research* 7, 101-105 (2015); published online (Epub) March (10.4168/aair.2015.7.2.101)). For a subset of patients, this barrier defect is associated with dysfunction in the tight-junction protein filaggrin (Bantz et al., *Journal of clinical & cellular immunology* 5, (2014); published online (Epub) April (10.4172/2155-9899.1000202)). Topical application to healthy mouse ears of the representative isolate of HV-CGN used in the human blister studies enhanced transcript levels of filaggrin compared to the AD-CGN isolate (FIG. 2C) without any noticeable change in ear erythema or thickness. Application of AD-CGN increased TEWL, while HV-CGN had no effect (FIG. 2D). Taken together, these data suggest that strains of CGN associated with a healthy status induce potentially beneficial immune outcomes related to activation of vitamin D, stimulation of innate immunity, and preservation of barrier function.

Example 6

CGN from Healthy Volunteers Improve Outcomes in a Mouse Model of AD

Figure 9:
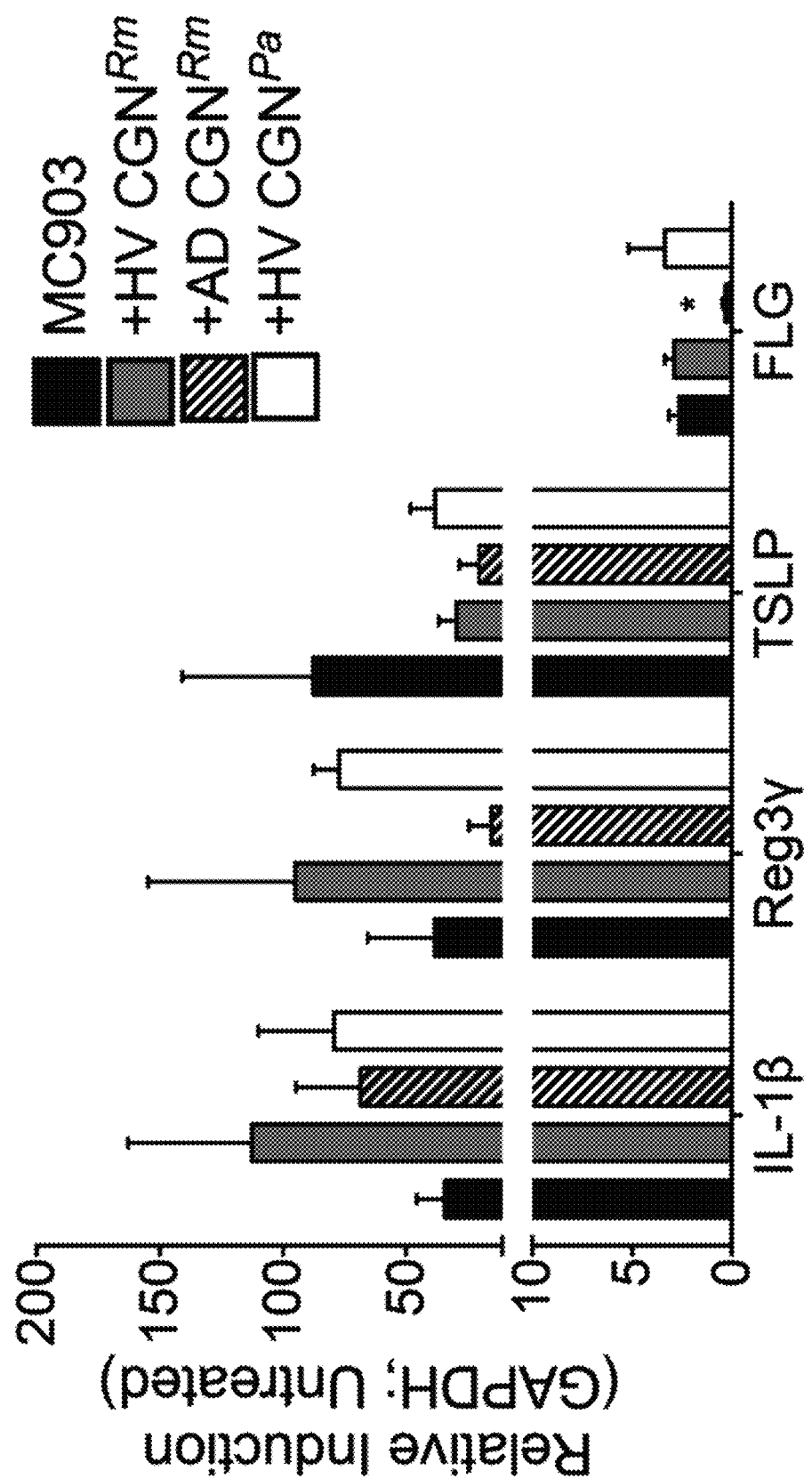
FIG. 9: CGN impact mouse filaggrin responses during MC903 challenge. Mice underwent MC903 treatment along with inoculation of gram negative isolates as shown. mRNA was harvested from ears on day 14 and analyzed by PCR. Data shown are representative of three independent experiments and displayed as mean+sem. Significant difference from MC903 shown as calculated by ANOVA. $*=p<0.05$.

MC903, a vitamin D analogue, induces an AD-like dermatitis when applied to mouse ears (22). Concurrent application of the HV-sourced *R. mucosa* isolate protected against onset of MC903-induced dermatitis as measured by ear thickness (FIG. 3A). In contrast, the AD-sourced *R. mucosa* isolate failed to protect against disease onset as did the HV-sourced *P. aeruginosa* (FIG. 3A), despite the latter's impact on KC activation (FIG. 7) and *S. aureus* inhibition (FIG. 1B). Application of the AD-sourced *R. mucosa* enhanced serum IgE induction, whereas the HV-sourced *R. mucosa* showed no significant impact (FIG. 3B). Consistent with inoculation of healthy mouse ears, transcript levels of filaggrin were significantly lower in MC903-treated mice exposed to AD-sourced *R. mucosa* (FIG. 9).

Figure 3D:
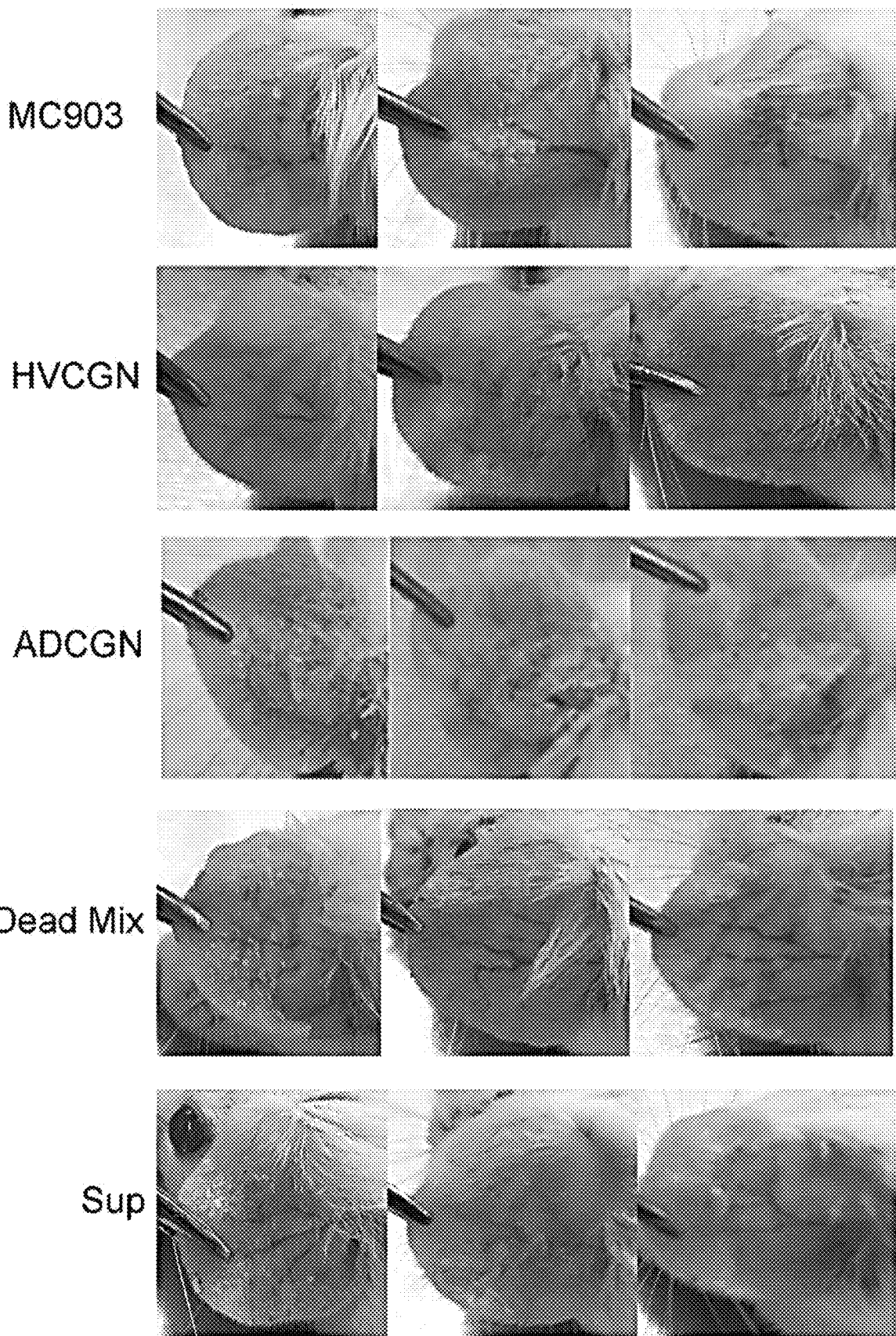

To test the therapeutic potential of CGN, AD-like dermatitis was induced with MC903 and then the ears were inoculated with CGN daily for three days. Treatment with HV-*R. mucosa* was associated with a reduction in ear thickness and visible redness (FIG. 3C-3D). To evaluate if a live biotherapeutic was necessary, or if surface and secreted factors alone could provide similar results, we applied an equivalent CFU concentration of lethally irradiated HV-CGN suspended in its supernatant. Neither this 'dead mix' nor the supernatant alone provided any benefit, and each increased ear thickness (FIG. 3C-3D).

While genome-wide linkage studies (Barnes et al., *J Allergy Clin Immunol* 125, 16-29 ell-11; quiz 30-11 (2010); published online (Epub) January (10.1016/j.jaci.2009.11.008)) and *S. aureus* characterization have elucidated the pathogenesis of AD, many causal underpinnings remain enigmatic. Current therapeutic approaches targeting host response and *S. aureus* colonization can significantly improve AD symptoms, yet even when successful, these treatments are not curative and extract a significant emotional toll on patients and their families (24). The studies disclosed herein evidence that the reported dysbiosis in AD is not simply an associated finding, but can be a contributor to pathology. Strains of *R. mucosa* isolated from healthy controls were able to influence many hallmarks of AD, improving barrier function, enhancing innate activation, and limiting *S. aureus* growth. Other gram negative bacteria could provide a similar effect.

Addition of gram negative *V. filiformis* lysates to skin creams may provide benefit in AD treatment (Gueniche et al., *The British journal of dermatology* 159, 1357-1363 (2008); published online (Epub) December (10.1111/j.1365-2133.2008.08836.x). However, the lack of efficacy of killed *R. mucosa* suggests that use of isolated secreted and/or surface products without live commensals may not provide benefit. Without being bound by theory, the dynamic interaction of host-commensal may be required for clinical utility of *R. mucosa*, and the potential for colonization offers the advantages of limited reapplications and more physiologic pharmacokinetics.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for culturing gram negative bacteria from skin, comprising:
   depositing a sample from skin of a subject in a liquid culture medium, wherein the liquid culture medium comprises a low nutrient medium containing essential nutrients for bacterial growth, an anti-gram positive bacterial agent, and an antifungal agent; and
   liquid culturing the sample in the liquid culture medium under conditions to inhibit growth of gram positive bacteria and fungi, thereby generating a population of cultured bacteria from the sample comprising at least one species of gram negative bacteria.

2. The method of claim 1, wherein the sample is from antecubital fossa of the skin of the subject.

3. The method of claim 1, wherein the subject does not have atopic dermatitis.

4. The method of claim 1, wherein the sample comprises gram negative bacteria and gram positive bacteria.

5. The method of claim 1, wherein the liquid culturing is followed by solid culturing on a plate.

6. The method of claim 1, wherein the at least one species of gram negative bacteria comprises *Acinetobacter radioresistens, Moraxella osloensis, Pantoea septica, Pseudomonas luteola, Pseudomonas aeruginosa*, or *Pseudomonas oryzihabitans*.

7. The method of claim 1, wherein the at least one species of gram negative bacteria comprises *Roseomonas mucosa*.

8. The method of claim 1, wherein the low nutrient medium is selected from the group consisting of Hank's balanced salt solution and Reasoner's 2A medium.

9. The method of claim 1, wherein the anti-gram positive bacterial agent is vancomycin.

10. The method of claim 1, wherein the antifungal agent is amphotericin B.

11. The method of claim 1, wherein the anti-gram positive bacterial agent is vancomycin, wherein the antifungal agent is amphotericin B, and wherein the low nutrient medium is selected from the group consisting of Hank's balanced salt solution and Reasoner's 2A media medium.

12. The method of claim 11, wherein the at least one species of gram negative bacteria comprises *Acinetobacter radioresistens, Moraxella osloensis, Pantoea septica, Pseudomonas luteola, Pseudomonas aeruginosa*, or *Pseudomonas oryzihabitans*.

13. The method of claim 11, wherein the at least one species of gram negative bacteria comprises *Roseomonas mucosa*.

14. The method of claim 1, wherein the subject is a human.

15. The method of claim 5, wherein the plate is an agar plate.

* * * * *